(12) United States Patent
Jones et al.

(10) Patent No.: US 8,026,265 B2
(45) Date of Patent: Sep. 27, 2011

(54) HETEROCYCLE SUBSTITUTED KETONE DERIVATIVES AS HISTONE DEACETYLASE (HDAC) INHIBITORS

(75) Inventors: Philip Jones, Pomezia (IT); Jesus Maria Ontoria Ontoria, Pomezia (IT); Rita Scarpelli, Pomezia (IT); Raffaele Ingenito, Pomezia (IT); Carsten Schultz-Fademrecht, Rome (IT)

(73) Assignee: Istituto de Ricerche di Biologia Molecolare P. Angeletti SpA., Pomezia Rome (IT)

( * ) Notice: Subject to any disclaimer, the term of this patent is extended or adjusted under 35 U.S.C. 154(b) by 448 days.

(21) Appl. No.: 12/086,812

(22) PCT Filed: Dec. 21, 2006

(86) PCT No.: PCT/GB2006/050472
§ 371 (c)(1),
(2), (4) Date: Jun. 19, 2008

(87) PCT Pub. No.: WO2007/072080
PCT Pub. Date: Jun. 28, 2007

(65) Prior Publication Data
US 2010/0234374 A1      Sep. 16, 2010

(30) Foreign Application Priority Data

Dec. 22, 2005  (GB) .................... 0526107.8

(51) Int. Cl.
*A61K 31/415* (2006.01)
*C07D 233/00* (2006.01)

(52) U.S. Cl. .................... 514/385; 548/300.1
(58) Field of Classification Search ............ 514/385; 548/300.1
See application file for complete search history.

(56) References Cited

U.S. PATENT DOCUMENTS

| | | |
|---|---|---|
| 4,075,217 A | 2/1978 | Gelotte et al. |
| 2008/0221157 A1 | 9/2008 | Chakravarty et al. |
| 2008/0262035 A1 | 10/2008 | Chakravarty et al. |
| 2009/0048228 A1 | 2/2009 | Attenni et al. |
| 2009/0156619 A1 | 6/2009 | Jones et al. |

FOREIGN PATENT DOCUMENTS

WO  WO2004/072047  8/2004

OTHER PUBLICATIONS

Ohta, et al., Chem. Pharm. Bull., 35(3), pp. 1058-1069, 1987.*
Huddleston, R., et al., "Enolate generation under hydrogenation conditions: Catalytic aldol cycloreduction of keto-enones", Organic Letters, vol. 5 (7), pp. 1143-1146 (2003).
Huddleston, R., et al., Organic Letters Supplementary Information, pp. S1-S40 (2003).
Trost, B., et al., "Ruthenium-catalyzed diyne hydrative cyclization: Synthesis of substituted 1,3-diene synthons", Organic Letters, vol. 7 (11), pp. 2097-2099 (2005).
Dixon, D., et al., "A new chemoselective base-mediated protection/deprotection method for aldehydes", Synlett, vol. 15, pp. 2317-2320 (2003).
Poirier, J., et al., Heterocycles, vol. 25, pp. 399-407 (1987).
Le Roux, C., Bull. Soc. Chim. Fr., vol. 130, pp. 832-842 (1993).
Owton, M., et al., Synthetic Communications, vol. 22 (3), pp. 351-357 (1992).
Miller, T., et al., "Histone Deacetylase Inhibitors", Journal of Medicinal Chemistry, vol. 46 (24), pp. 5097-5116 (2003).
Notice of Allowance mailed Aug. 26, 2010 in U.S. Appl. No. 11/792,294.

* cited by examiner

*Primary Examiner* — Susannah Chung
(74) *Attorney, Agent, or Firm* — Li Su; David A. Muthard

(57) ABSTRACT

The present invention relates to compounds of formula (I): and pharmaceutically acceptable salts and tautomers thereof. Compounds of the present invention are inhibitors of histone deacetylase (HDAC) and are useful for treating cellular proliferative diseases, including cancer. They are also useful for treating neurodegenerative diseases, mental retardation, schizophrenia, inflammatory diseases, restenosis, immune disorders, diabetes, cardiovascular disorders and asthma.

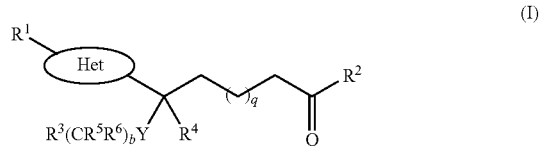

(I)

7 Claims, No Drawings

HETEROCYCLE SUBSTITUTED KETONE DERIVATIVES AS HISTONE DEACETYLASE (HDAC) INHIBITORS

The present invention relates to heterocycle substituted ketone derivatives that are inhibitors of histone deacetylase (HDAC). The compounds of the present invention are useful for treating cellular proliferative diseases, including cancer. Further, the compounds of the present invention are useful for treating neurodegenerative diseases, schizophrenia and stroke among other diseases.

In eukaryotic cells the orderly packaging of DNA in the nucleus plays an important role in the regulation of gene transcription. Nuclear DNA is ordered in a compact complex called chromatin. The core of the complex is an octamer of highly conserved basic proteins called histones. Two each of histones H2A, H2B, H3 and H4 associate and DNA winds around the basic amino acids of the histones interacting with the negatively charged phosphate groups of the DNA. One molecule of histone H1 is associated with each wound core which accommodates approximately 146 by of DNA. The cores are, in turn, packaged into a compact regular structure with about 200 by of DNA between each core.

The amino-terminal tails of the histones are subject to post-translational modification, in particular by acetylation of lysine. Histone deacetylases (HDACs) and histone acetyl transferases (HATs) determine the pattern of histone acetylation, which together with other dynamic sequential post-translational modifications might represent a 'code' that can be recognised by non-histone proteins forming complexes involved in the regulation of gene expression. This and the ability of histone deacetylases (HDACs) to also modify non-histonic substrates and participate in multi-protein complexes contributes to the regulation of gene transcription, cell cycle progression and differentiation, genome stability and stress responses.

Eleven members of the HDAC family have been identified in humans, which share a conserved catalytic domain and are grouped into two classes: class I (1, 2, 3, 8), homologous to yeast Rpd3; class IIa (4, 5, 7, 9) and IIb (6, 10), homologous to yeast Hdal. HDAC11 shares homologies with both classes, but is at the same time distinct from all the other ten subtypes. Interest in these enzymes is growing because HDAC inhibitors (HDACi) are promising therapeutic agents against cancer and other diseases. The first generation of HDACi were discovered from cell-based functional assays and only later identified as HDAC class I/II inhibitors. Present HDAC inhibitors are pan-specific or poorly selective. Those that entered clinical trials all show similar adverse effects, mainly fatigue, anorexia, hematologic and GI-toxicity, that becomes dose-limiting in clinical trials. It is not at all clear whether the antitumor properties of HDAC inhibitors are due to their lack of specificity or are the consequence of hitting one or few "crucial" subtypes. This question is of considerable interest because it may open the way for the development of novel, more sensitive compounds with possibly enhanced efficacy and/or tolerability. More recent studies were therefore directed to better define the biological function of different class members and to devise subtype-selective enzymatic assays to assist in the development of improved cancer chemotherapies.

The class IIa HDACs contain a highly conserved C-terminal catalytic domain (~420 amino acids) homologous to yHDA1 and an N-terminal domain with no similarity to other proteins. The activity of the class IIa HDACs is regulated at several levels, including tissue-specific gene expression, recruitment of distinct cofactors and nucleocytoplasmic shuffling. Whereas most class I HDACs are ubiquitously expressed, class IIa HDACs are expressed in a restricted number of cell types.

HDAC inhibitors cause the induction of differentiation, growth arrest and/or apoptosis in a broad spectrum of transformed cells in culture and tumours in animals, including both haematological cancers and solid tumours. These inhibitory effects are believed to be caused, in part, by accumulation of acetylated proteins, such as nucleosomal histones, which appear to play a major role in regulation of gene transcription. A proposed mechanism for the anti-tumour effects of HDAC inhibitors is that the accumulation of acetylated histones leads to activation (and repression) of the transcription of a select number of genes whose expression causes inhibition of tumour cell growth. Expression profiling of cells cultured with HDAC inhibitors supports this model, as studies demonstrate that the expression of a small number of genes (2-5% of the expressed genes) is altered (activated or repressed). The mechanism of gene repression or activation is not well understood and might result from either direct or indirect effects of histone acetylation or from the increase in acetylation of proteins other than histones (e.g. transcription factors).

There is still much to be understood about the family of HDACs, including the varying functions of different HDACs and the range of HDAC substrates. The development of selective HDAC inhibitors might be important in defining their biological role and potential as therapeutic agents. Clinically, the optimal dose, timing and duration of therapy, as well as the most appropriate agents to combine with HDAC inhibitors, are still to be defined.

The compounds of this invention are useful in the inhibition of histone deacetylase, particularly class I histone deacetylase. The compounds are HDAC 1 and HDAC 3 inhibitors. A subset of compounds of this invention is also active against other HDAC subtypes such as HDAC 2.

The present invention provides compounds of formula I:

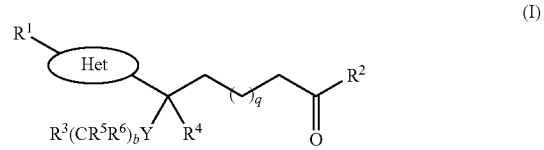

wherein:
b is 0, 1, 2, 3, 4 or 5;
q is 1, 2, 3 or 4;
Y is C=O, (C=O)NR$^7$, O(C=O)NR$^7$ or (CH$_2$)$_a$O;
a is 0, 1, 2 or 3;
Het is a 5 membered unsaturated heterocycle containing 1, 2, 3 or 4 heteroatoms independently selected from N, O and S, but not more than one of which is O or S, or a 6 membered unsaturated heterocycle containing 1, 2, 3 or 4 heteroatoms independently selected from N and O; optionally substituted by one or more groups independently chosen from cyano, halogen, hydroxy, oxo, nitro, amino, C$_{1-6}$alkylamino, di(C$_{1-6}$alkyl)amino, C$_{1-6}$alkyl, haloC$_{1-6}$alkyl, C$_{1-6}$alkoxy, haloC$_{1-4}$alkoxy, C$_{3-10}$cycloalkyl, C$_{2-6}$alkenyl, C$_{2-6}$alkynyl and C$_{6-10}$aryl;
R$^1$ hydrogen, C$_{1-6}$alkyl, haloC$_{1-6}$alkyl, C$_{6-10}$aryl, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-10 membered unsaturated or partially saturated heterocycle containing heteroatoms independently selected from O, N and S; any of which rings being optionally substituted by one or more groups independently chosen from cyano, halogen, nitro, oxo, hydroxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, carboxy, $C_{6-10}$aryl, $C_{6-10}$aryloxy, $C_{6-10}$arylcarbonyl and $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl;

$R^2$ is $C_{1-6}$alkyl;

$R^3$ is hydrogen, halogen, hydroxy, cyano, $C_{1-6}$alkyl, halo$C_{1-6}$alkyl, $C_{1-6}$alkoxy, halo$C_{1-6}$alkoxy, $C_{3-10}$cycloalkyl, halo$C_{3-10}$cycloalkyl, $C_{2-10}$alkenyl, $C_{2-10}$alkynyl, nitro, $N(R^a)_2$ wherein $R^a$ is independently selected from hydrogen, $C_{1-6}$alkyl and $C_{1-6}$alkylcarbonyl; $C_{6-10}$aryl, $C_{6-10}$aryl$C_{1-6}$alkyl, $C_{6-10}$-aryl$C_{1-6}$alkoxy, 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independently selected from N, O or S; any of which rings being optionally substituted by one or more groups independently chosen from $R^b$;

$R^4$ is hydrogen or $C_{1-6}$alkyl; or $R^4$ together with Y—$(CR^5R^6)_b$—$R^3$ forms an oxo group;

$R^5$ and $R^6$ are independently hydrogen or $C_{1-6}$alkyl;

$R^7$ is hydrogen or $C_{1-6}$alkyl;

each $R^b$ is halogen, hydroxy, cyano, $C_{1-6}$alkyl, halo$C_{1-6}$alkyl, halo$C_{1-6}$alkylcarbonyl, halo$C_{1-6}$alkylcarbonyloxy, $C_{1-6}$alkoxy, halo$C_{1-6}$alkoxy, carboxy, $C_{1-6}$alkylcarbonyl, $C_{1-6}$alkoxycarbonyl, nitro, oxo, $SO_2N(R^c)_2$, $N(R^c)_2$ wherein $R^c$ is independently selected from hydrogen, $C_{1-6}$alkyl, $C_{1-6}$alkylcarbonyl, carboxy and $C_{1-6}$alkoxycarbonyl, or $C_{6-10}$aryl, $C_{6-10}$-aryl$C_{1-6}$alkyl, 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy;

or a pharmaceutically acceptable salt or tautomer thereof.

b is preferably 0, 1, 2 or 3. More particularly b is 0, 1 or 2.

q is preferably 2, 3 or 4, especially 3 or 4, and most especially 3.

Y is preferably C=O, (C=O)/NH, O(C=O)NH, O or $(CH_2)O$. A further preferred Y group is (C=O)NMe.

In an embodiment Y is or C=O or (C=O)$NR^7$.

In another embodiment Y is C=O.

In another embodiment Y is (C=O)$NR^7$. In another embodiment Y is O(C=O)$NR^7$.

Preferably, $R^7$ is hydrogen or methyl. More particularly, $R^7$ is hydrogen.

In another embodiment Y is $(CH_2)_aO$.

a is preferably 0, 1 or 2. More particularly a is 0 or 1.

Preferably, Het is an optionally substituted 5 membered unsaturated heterocycle containing 1, 2, 3 or 4 heteroatoms independently selected from N, O and S, but not more than one of which is O or S.

In an embodiment Het is an optionally substituted imidazolyl, oxazolyl, triazolyl, thienyl, furyl, oxadiazolyl, thiazolyl or pyrazolyl. In another embodiment Het is an optionally substituted imidazolyl or thiazolyl.

Preferably, Het is an optionally substituted imidazolyl.

Preferably Het is unsubstituted or substituted by one, two or three groups. More particularly Het is unsubstituted or monosubstituted. Favoured optional substituents include $C_{1-4}$alkyl and $C_{6-10}$aryl, especially methyl and phenyl.

In one embodiment Het is unsubstituted.

For the avoidance of doubt $R^1$ may be attached to any substitutable position of Het as may any optional substituent on Het.

Thus, particular preferred Het groups include imidazolyl, methylimidazolyl, phenylimidazolyl, phenyloxazolyl, triazolyl, thienyl, furyl, oxadiazolyl, thiazolyl, oxazolyl and pyrazolyl. In an embodiment, Het is imidazolyl or thiazolyl. More particularly Het is imidazolyl.

Specific Het groups are imidazol-2-yl, 1,3-thiazol-5-yl, and imidazol-4-yl. More specifically, Het is imidazol-2-yl or imidazol-4-yl.

Preferably, $R^1$ is an optionally substituted ring selected from $C_{6-10}$aryl, a 5 membered unsaturated heterocycle containing 1, 2 or 3 heteroatoms independently selected from N, O and S, but not more than one of which is O or S, a 6 membered unsaturated heterocycle containing 1, 2 or 3 nitrogen atoms, or a 8, 9 or 10 membered unsaturated or partially saturated heterocycle containing 1, 2, 3 or 4 heteroatoms independently selected from O, N and S.

More particularly, $R^1$ is an optionally substituted phenyl, naphthyl, thienyl, isoxazolyl, pyridinyl, benzothienyl, thiazolotriazolyl, dihydrobenzodioxinyl, benzothiazolyl, quinolinyl, isoquinolinyl, quinoxalinyl, tetrahydroisoquinolinyl, indolyl, naphthyridinyl or dihydroquinolinyl.

Favourably $R^1$ is unsubstituted or substituted by one, two or three groups. More particularly $R^1$ is unsubstituted, monosubstituted or disubstituted. Favoured optional substituents include cyano, halogen, $C_{1-4}$alkyl, halo$C_{1-4}$alkyl, $C_{1-4}$alkoxy, halo$C_{1-4}$alkoxy, $C_{6-10}$aryl, carboxy, nitro, hydroxy and oxo. Examples of typical optional substituents include cyano, bromine, chlorine, fluorine, methyl, trifluoromethyl, methoxy, difluoromethoxy, phenyl, carboxy, nitro, trifluoromethoxy, hydroxy and oxo.

In an embodiment $R^1$ is unsubstituted.

Thus, particular preferred $R^1$ groups include phenyl, cyanophenyl, bromophenyl, chlorophenyl, dichlorophenyl, fluorophenyl, difluorophenyl, trifluoromethylphenyl, bis(trifluoromethyl)phenyl, methoxyphenyl, difluoromethoxyphenyl, biphenyl, naphthyl, thienyl, phenylisoxazolyl, pyridinyl, (chloro)(methyl)benzothienyl, (methyl)(trifluoromethyl)thiazolotriazolyl, benzothienyl, dihydrobenzodioxinyl, benzothiazolyl, methoxyquinolinyl, quinolinyl, isoquinolinyl, quinoxalinyl, methoxynaphthyl, tetrahydroisoquinolinyl, methylquinolinyl, indolyl, (dimethylamino)phenyl, (fluoro)(methoxy)phenyl, carboxyphenyl, dimethoxynaphthyl, nitrophenyl, (trifluoromethoxy)phenyl, ethoxyphenyl, (acetylamino)phenyl, (methoxycarbonyl)phenyl, aminophenyl, dimethoxyphenyl, (fluoro)(trifluoromethyl)phenyl, hydroxyphenyl, (fluoro)quinolinyl, quinoxalinyl, naphthyridinyl, and (oxo)dihydroquinolinyl.

In an embodiment $R^1$ is an optionally substituted $C_{6-10}$aryl.

In an embodiment $R^1$ is phenyl or naphthyl.

Specific $R^1$ groups are phenyl and 2-naphthyl.

$R^2$ is preferably methyl, ethyl, propyl or butyl. More particularly, $R^2$ is methyl or ethyl.

$R^3$ is preferably hydrogen, hydroxy, $C_{1-6}$alkyl, halo$C_{1-6}$alkyl, $C_{1-6}$alkoxy, $C_{3-10}$cycloalkyl, acetylamino, amino, $C_{1-6}$alkylamino, di($C_{1-6}$alkyl)amino, $C_{6-10}$aryl, $C_{6-10}$-aryl$C_{1-6}$alkoxy; a 4, 5 or 6 membered saturated or partially saturated heterocycle containing 1, 2 or 3 heteroatoms independently selected from N, O and S, optionally bridged by a $C_{1-4}$alkyl group; a 5 membered unsaturated heterocycle containing 1, 2, 3 or 4 heteroatoms independently selected from N, O and S, but not more than one of which is O or S; a 6 membered unsaturated heterocycle containing 1, 2 or 3 nitrogen atoms; or a 8-13 membered saturated, partially saturated or unsaturated heterocycle containing 1, 2, 3 or 4 heteroatoms independently selected from N, O and S; any of which rings being optionally substituted by one or more groups independently chosen from $R^b$.

In an embodiment $R^3$ is hydrogen, dimethylamino, phenyl, naphthyl, pyrrolidinyl, piperidinyl, azoniabicyclo[2.2.1]heptanyl, azoniabicyclo[2.2.2]octanyl, piperazinyl, morpholinyl, thienyl, thiazolyl, imidazolyl, pyrazolyl, isoxazolyl, thiadiazolyl, pyridinyl, indolyl, benzothienyl, benzothiadiazolyl, benzoxadiazolyl, dihydrobenzofuryl, dihydrothiazolopyrimidinyl, isoquinolyl, dihydrobenzodioxinyl, dihydrobenzoxazinyl, tert-butoxy, cyclopentyl, methyl, trifluoromethyl, methoxy, diethylamino, hydroxy, benzimidazolyl, benzofuranyl, triazolopyrimidinyl, dihydrobenzoxazolyl, dihydroindolyl, dihydroquinazolinyl, dihydrophthalazinyl, indazolyl, quinolinyl, benzisoxazolyl, benzotriazolyl, tetrahydrobetacarbolinyl, dihydroisoindolyl, tetrahydronaphthyridinyl, tetrazolyl, benzyloxy, thiomorpholinyl, azetidinyl, tetrahydroquinolinyl, acetylamino, triazolyl, thiazolidinyl or amino; any of which rings being optionally substituted by one or more groups independently chosen from $R^b$.

Preferably, $R^3$ is hydrogen, hydroxy, phenyl, piperazinyl, quinolinyl, tetrahydroquinolinyl, thiazolyl, pyridinyl, morpholinyl, pyrazolyl, pyrrolidinyl, methoxy, dimethylamino, acetylamino, triazolyl, thiazolidinyl, amino or methyl; any of which rings being optionally substituted by one or more groups independently chosen from $R^b$ In an embodiment, when $R^3$ is a ring it is unsubstituted or substituted by one, two or three groups selected from $R^b$. Preferably, when $R^3$ is a ring it is unsubstituted or monosubstituted.

Favoured $R^b$ groups include halogen, cyano, $C_{1-6}$alkyl, $C_{1-6}$alkoxy, halo$C_{1-6}$alkoxy, carboxy, $C_{1-6}$alkoxycarbonyl, nitro, aminosulfonyl, ($C_{1-6}$alkylcarbonyl)amino, morpholinyl, piperazinyl, thiazolyl, pyrazolyl, isoxazolyl, pyridinyl, oxo, halo$C_{1-6}$alkyl, phenyl, pyrrolidinyl or benzyl; any of which rings being optionally substituted by one or more groups independently chosen from $C_{1-6}$alkyl and halo$C_{1-6}$alkyl.

In an embodiment, when $R^b$ is a ring it is unsubstituted or substituted by one, two or three independently selected groups.

In an embodiment $R^b$ is $C_{1-6}$alkyl, $C_{6-10}$aryl or $C_{6-10}$aryl$C_{1-6}$alkyl.

Particular $R^b$ groups include methyl, phenyl and benzyl.

Preferably, $R^3$ is hydrogen, hydroxy, phenyl, methylpiperazinyl, phenylpiperazinyl, quinolinyl, piperidinyl, benzylpiperidinyl, tetrahydroquinolinyl, thiazolyl, pyridinyl, morpholinyl, pyrazolyl, methylpiperidinyl, methylpyrrolidinyl, methoxy, dimethylamino, acetylamino, triazolyl, pyrrolidinyl, thiazolidinyl, amino or methyl.

Specific $R^3$ groups include hydrogen, hydroxy, phenyl, 1-methylpiperazin-4-yl, 1-phenylpiperazin-4-yl, quinolin-6-yl, piperidin-1-yl, 1-benzylpiperidin-4-yl, 3,4-dihydroquinolin-1(2H)-yl, 1,3-thiazol-2-yl, pyridin-3-yl, pyridin-4-yl, pyridin-2-yl, morpholin-4-yl, 1H-pyrazol-1-yl, 1H-pyrazol-4-yl, 1-methylpiperidin-3-yl, 1-methylpiperidin-2-yl, 1-methylpyrrolidin-3-yl, methoxy, dimethylamino, acetylamino, 4H-1,2,4-triazol-4-yl, pyrrolidin-1-yl, 1-methylpiperidin-4-yl, 1,3-thiazolidin-3-yl, amino and methyl.

$R^4$ is preferably hydrogen or methyl; or $R^4$ together with $Y(CR^5R^6)_bR^3$ forms an oxo group.

In an embodiment $R^4$ is hydrogen or $C_{1-6}$alkyl.

In another embodiment $R^4$ is hydrogen or methyl.

Preferably, $R^5$ and $R^6$ are independently selected from hydrogen and $C_{1-4}$alkyl. Particularly, $R^5$ and $R^6$ are independently selected from hydrogen and methyl.

In an embodiment $R^5$ and $R^6$ are both hydrogen.

In an embodiment $R^a$ is hydrogen or $C_{1-6}$alkyl.

In an embodiment $R^c$ is hydrogen or $C_{1-6}$alkyl

Preferably, each $R^d$ is independently selected from hydrogen, methyl and acetyl.

Preferably, the α1 carbon asymmetric center of the compounds of the present invention has the stereochemical configuration of S. In one embodiment the α1 carbon asymmetric center has the stereochemical configuration of R.

The present invention also provides compounds of formula II:

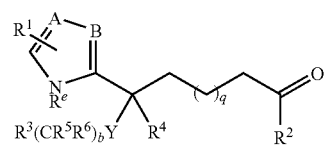

(II)

wherein:
b, q, $R^1$, $R^2$, $R^3$, $R^4$, $R^5$, $R^6$ and Y are as defined above for formula I;
one of A and B is N and the other CH;
$R^e$ is hydrogen or $C_{1-6}$alkyl;
or a pharmaceutically acceptable salt or tautomer thereof.

The preferred identities with reference to formula II are as defined previously mutate mutandis. $R^e$ is preferably hydrogen or methyl. More particularly $R^e$ is hydrogen.

The present invention also provides compounds of formula III:

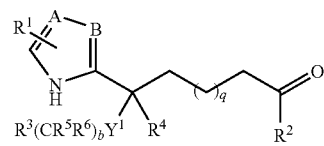

(III)

wherein:
$Y^1$ is (C=O) or (C=O)$NR^7$;
$R^1$, $R^2$, $R^3$, $R^5$, $R^6$, b and q are as defined for formula I;
one of A and B is N and the other CH;
$R^4$ is hydrogen or $C_{1-6}$alkyl;
or a pharmaceutically acceptable salt or tautomer thereof.

The preferred identities with reference to formula III are as defined previously for formula I mutatis mutandis.

For the avoidance of doubt, $R^1$ may be attached to any substitutable position of the ring in the compounds of formulae II or III.

In an embodiment A is N and B is CH.

In another embodiment A is CH and B is N.

In an embodiment, $R^3$ is hydroxy, phenyl, methylpiperazinyl, phenylpiperazinyl, quinolinyl, piperidinyl, benzylpiperidinyl, tetrahydroquinolinyl, thiazolyl, pyridinyl, morpholinyl, pyrazolyl, methylpiperidinyl, methylpyrrolidinyl, methoxy, dimethylamino, amino, acetylamino, triazolyl, pyrrolidinyl, thiazolidinyl and methyl.

In another embodiment, $R^3$ groups include hydroxy, phenyl, 1-methylpiperazin-4-yl, 1-phenylpiperazin-4-yl, quinolin-6-yl, piperidin-1-yl, 1-benzylpiperidin-4-yl, 3,4-dihydroquinolin-1(2H)-yl, 1,3-thiazol-2-yl, pyridin-3-yl, pyridin-4-yl, pyridin-2-yl, morpholin-4-yl, 1H-pyrazol-1-yl, 1H-pyrazol-4-yl, 1-methylpiperidin-3-yl, 1-methylpiperidin-2-yl, 1-methylpyrrolidin-3-yl, methoxy, dimethylamino, acetylamino, 4H-1,2,4-triazol-4-yl, pyrrolidin-1-yl, amino, 1-methylpiperidin-4-yl, 1,3-thiazolidin-3-yl and methyl.

$R^4$ is preferably hydrogen or methyl.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

The compounds may exist in different isomeric forms, all of which are encompassed by the present invention.

When any variable (e.g. $R^5$ and $R^6$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched and straight-chain saturated aliphatic hydrocarbon groups having the specified number of carbon atoms. For example, "$C_{1-6}$ alkyl" is defined to include groups having 1, 2, 3, 4, 5 or 6 carbons in a linear or branched arrangement. For example, "$C_{1-6}$ alkyl" specifically includes methyl, ethyl, n-propyl, i-propyl, n-butyl, t-butyl, i-butyl, pentyl, hexyl, and so on. The preferred alkyl group is methyl. The term "cycloalkyl" means a monocyclic, bicyclic or polycyclic saturated aliphatic hydrocarbon group having the specified number of carbon atoms. For example, "$C_{7-10}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl.

"Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy and t-butoxy. The preferred alkoxy group is methoxy. The term '$C_{6-10}$aryloxy' can be construed analogously, and an example of this group is phenoxy.

The terms "halo$C_{1-6}$alkyl" and "halo$C_{1-6}$alkoxy" mean a $C_{2-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$. The term "halo$C_{3-10}$cycloalkyl" can be construed in an analogous manner.

The term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$.

The term "$C_{1-6}$alkylcarbonyl" or "$C_{1-6}$alkoxycarbonyl" denotes a $C_{1-6}$alkyl or $C_{1-6}$alkoxy radical, respectively, attached via a carbonyl (C=O) radical. Suitable examples of $C_{1-6}$alkylcarbonyl groups include methylcarbonyl, ethylcarbonyl, propylcarbonyl, isopropylcarbonyl and tert-butylcarbonyl. Examples of $C_{1-6}$alkoxycarbonyl include methoxycarbonyl, ethoxycarbonyl, propoxycarbonyl, isopropoxycarbonyl and tert-butoxycarbonyl. The term '$C_{6-10}$arylcarbonyl' can be construed analogously, and an example of this group is benzoyl.

As used herein, the term "$C_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. The straight or branched portion of the alkenyl group may contain double bonds and may be substituted if a substituted alkenyl group is indicated. Preferred alkenyl groups include ethenyl and propenyl.

The term "$C_{2-6}$alkynyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. The straight or branched portion of the alkynyl group may contain triple bonds and may be substituted if a substituted alkynyl group is indicated. Preferred alkynyl groups include ethynyl and propynyl.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl, tetrahydrobenzo[7]annulene, indenyl and tetrahydroindenyl. The preferred aryl group is phenyl or naphthyl, especially phenyl.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furanyl, furazanyl, imidazolyl, indolinyl, indolyl, indolizinyl, indolinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyridin-2-onyl, pyrrolidinyl, imidazolyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydroisochromenyl, dihydroimidazolonyl, dihydrotriazolonyl, dihydrobenzodioxinyl, dihydrothiazolopyrimidinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, quinazolinyl, pteridinyl, dihydroquinazolinyl, dihydrophthalazinyl, dihydroisoindolyl, tetrahydronaphthyridinyl, tetrahydrobetacarbolinyl, dibenzofuranyl, naphthyridinyl, dihydrochromenyl, dihydrobenzothiazolyl, imidazothiazolyl, tetrahydroindazolyl, tetrahydrobenzothienyl, hexahydronaphthyridinyl, tetrahydropyridonaphthyridinyl, tetrahydroimidazopyridinyl, tetrahydroimidazopyrazinyl, pyrrolopyridinyl and N-oxides thereof.

Attachment of a heterocyclyl substituent can occur via a carbon atom or via a heteroatom.

A preferred 4 membered saturated heterocycle is azetidinyl.

Preferred 5 or 6 membered saturated or partially saturated heterocycles are pyrrolidinyl, piperidyl, piperazinyl, morpholinyl, azoniabicyclo[2.2.1]heptanyl, azoniabicyclo[2.2.2]octanyl and thiomorpholinyl.

Preferred 5 membered unsaturated heterocycles are thienyl, thiazolyl, pyrazolyl, isoxazolyl, imidazolyl, thiadiazolyl, oxazolyl, triazolyl, tetrazolyl, furyl and oxadiazolyl.

A preferred 6 membered unsaturated heterocycle is pyridinyl. Further preferred rings are pyrimidinyl, pyridazinyl and pyrazinyl.

Preferred 8-10 membered saturated, partially saturated or unsaturated heterocycles are benzothienyl, isoquinolyl, indolyl, benzothiadiazolyl, benzoxadiazolyl, thiazolotriazolyl, dihydrobenzodioxinyl, dihydrothiazolopyrimidinyl, dihydrobenzoxazinyl, dihydrobenzofuranyl, benzothiazolyl, quinolinyl, isoquinolinyl, benzimidazolyl, benzofuranyl, dihydrobenzoxazolyl, dihydroindolyl, dihydroquinazolinyl, dihydrophthalazinyl, indazolyl, benzisoxazolyl, benzotriazolyl, dihydroisoindolyl, tetrahydronaphthyridinyl, triazolopyrimidinyl, quinoxalinyl, tetrahydroisoquinolinyl, naphthyridinyl, dihydroquinolinyl, dihydroisochromenyl, dihydrochromenyl, tetrahydroquinolinyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl and pyrrolopyridinyl.

A preferred 13 membered partially saturated heterocycle is tetrahydrobetacarbolinyl.

As used herein, the term 'halogen' refers to fluorine, chlorine, bromine and iodine, of which fluorine, chlorine and bromine are preferred.

Particular compounds within the scope of the present invention include:

2-[5-(2-naphthyl)-1H-imidazol-2-yl]-8-oxodecanoic acid;

5-(2-naphthyl)-2-(7-oxo-1-{[(2-phenylethyl)amino]carbonyl}nonyl)-1H-imidazol-1-ium trifluoroacetate;

2-[1-(hydroxymethyl)-7-oxononyl]-5-(2-naphthyl)-1H-imidazol-1-ium trifluoroacetate;

5-(2-naphthyl)-2-{7-oxo-1-[(pyridin-3-ylmethoxy)methyl]nonyl}-1H-imidazol-1-ium trifluoroacetate;

5-(2-naphthyl)-2-(8-oxononanoyl)-1H-imidazol-1-ium trifluoroacetate;

9-hydroxy-9-[5-(2-naphthyl)-1H-imidazol-2-yl]nonan-3-one;

(−)-9-hydroxy-9-[5-(2-naphthyl)-1H-imidazol-2-yl]nonan-3-one;

2-(1-Hydroxy-1-methyl-7-oxononyl)-5-(2-naphthyl)-1H-imidazol-1-ium trifluoroacetate;

2-(1-methoxy-7-oxononyl)-5-(2-naphthyl)-1H-imidazol-1-ium trifluoroacetate;

5-(2-naphthyl)-2-{7-oxo-1-[({[(1S)-1-phenylethyl]amino}carbonyl)oxy]nonyl}-1H-imidazol-1-ium trifluoroacetate;

2-[1-(anilinocarbonyl)-7-oxononyl]-5-(2-naphthyl)-1H-imidazol-1-ium trifluoroacetate;

2-{1-[(benzylamino)carbonyl]-7-oxononyl}-5-(2-naphthyl)-1H-imidazol-1-ium trifluoroacetate;

1-methyl-4-{2-[5-(2-naphthyl)-1H-imidazol-1-ium-2-yl]-8-oxodecanoyl}piperazin-1-ium bis(trifluoroacetate);

4-{2-[5-(2-naphthyl)-1H-imidazol-1-ium-2-yl]-8-oxodecanoyl}-1-phenylpiperazin-1-ium bis(trifluoroacetate);

2-(1-{[methyl(quinolin-6-ylmethyl)amino]carbonyl}-7-oxononyl)-5-(2-naphthyl)-1H-imidazol-1-ium trifluoroacetate;

1-[2-({2-[5-(2-naphthyl)-1H-imidazol-1-ium-2-yl]-8-oxodecanoyl}amino)ethyl]piperidinium bis(trifluoroacetate);

1-benzyl-4-({2-[5-(2-naphthyl)-1H-imidazol-1-ium-2-yl]-8-oxodecanoyl}amino)piperidinium bis(trifluoroacetate);

2-[1-({[2-(3,4-dihydroquinolin-1(2H)-yl)ethyl]amino}carbonyl)-7-oxononyl]-5-(2-naphthyl)-1H-imidazol-1-ium trifluoroacetate;

1-[1,1-dimethyl-2-({2-[5-(2-naphthyl)-1H-imidazol-1-ium-2-yl]-8-oxodecanoyl}amino)ethyl]piperidinium bis(trifluoroacetate);

5-(2-naphthyl)-2-(7-oxo-1-{[(1,3-thiazol-2-ylmethyl)amino]carbonyl}nonyl)-1H-imidazol-1-ium trifluoroacetate;

5-(2-naphthyl)-2-(7-oxo-1-{[(pyridin-3-ylmethyl)amino]carbonyl}nonyl)-1H-imidazol-1-ium trifluoroacetate;

5-(2-naphthyl)-2-{7-oxo-1-[(pyridin-3-ylamino)carbonyl]nonyl}-1H-imidazol-1-ium trifluoroacetate;

5-(2-naphthyl)-2-{7-oxo-1-[(1,3-thiazol-2-ylamino)carbonyl]nonyl}-1H-imidazol-1-ium trifluoroacetate;

5-(2-naphthyl)-2-(7-oxo-1-{[(2-pyridin-4-ylethyl)amino]carbonyl}nonyl)-1H-imidazol-1-ium trifluoroacetate;

5-(2-naphthyl)-2-(7-oxo-1-{[(2-pyridin-2-ylethyl)amino]carbonyl}nonyl)-1H-imidazol-1-ium trifluoroacetate;

4-[2-({2-[5-(2-naphthyl)-1H-imidazol-1-ium-2-yl]-8-oxodecanoyl}amino)ethyl]morpholin-4-ium bis(trifluoroacetate);

1-[2-({2-[5-(2-naphthyl)-1H-imidazol-1-ium-2-yl]-8-oxodecanoyl}amino)ethyl]-1H-pyrazol-1-ium bis(trifluoroacetate);

4-[2-({5-[5-(2-naphthyl)-1H-imidazol-1-ium-2-yl]-8-oxodecanoyl}amino)ethyl]-1H-pyrazol-1-ium bis(trifluoroacetate);

1-methyl-3-[({2-[5-(2-naphthyl)-1H-imidazol-1-ium-2-yl]-8-oxodecanoyl}amino)methyl]piperidinium bis(trifluoroacetate);

1-methyl-4-[({2-[5-(2-naphthyl)-1H-imidazol-1-ium-2-yl]-8-oxodecanoyl}amino)methyl]piperidinium bis(trifluoroacetate);

1-methyl-2-[(methyl{2-[5-(2-naphthyl)-1H-imidazol-1-ium-2-yl]-8-oxodecanoyl}amino)methyl]piperidinium bis(trifluoroacetate);

2-[1-({[(1-methylpyrrolidinium-3-yl)methyl]amino}carbonyl)-7-oxononyl]-5-(2-naphthyl)-1H-imidazol-1-ium bis(trifluoroacetate);

2-(1-{[(2-methoxyethyl)amino]carbonyl}-7-oxononyl)-5-(2-naphthyl)-1H-imidazol-1-ium trifluoroacetate;

2-[1-({[2-(dimethylammonio)ethyl]amino}carbonyl)-7-oxononyl]-5-(2-naphthyl)-1H-imidazol-1-ium bis(trifluoroacetate);

2-[1-({[2-(acetylamino)ethyl]amino}carbonyl)-7-oxononyl]-5-(2-naphthyl)-1H-imidazol-1-ium trifluoroacetate;

4-[2-({2-[5-(2-naphthyl)-1H-imidazol-1-ium-2-yl]-8-oxodecanoyl}amino)ethyl]-4H-1,2,4-triazol-4-ium bis(trifluoroacetate);

5-(2-naphthyl)-2-(7-oxo-1-{[(2-pyrrolidinium-1-ylethyl)amino]carbonyl}nonyl)-1H-imidazol-1-ium bis(trifluoroacetate);

1-methyl-4-({2-[5-(2-naphthyl)-1H-imidazol-1-ium-2-yl]-8-oxodecanoyl}amino)piperidinium bis(trifluoroacetate);

5-(2-naphthyl)-2-[7-oxo-1-(1,3-thiazolidin-3-ylcarbonyl)nonyl]-1H-imidazol-1-ium trifluoroacetate;

5-(2-naphthyl)-2-(7-oxo-1-{[(2-pyridin-3-ylethyl)amino]carbonyl}nonyl)-1H-imidazol-1-ium trifluoroacetate;

2-[1-(aminocarbonyl)-7-oxononyl]-5-(2-naphthyl)-1H-imidazol-1-ium trifluoroacetate;

2-{1-[(methylamino)carbonyl]-7-oxononyl}-5-(2-naphthyl)-1H-imidazol-1-ium trifluoroacetate;

1-(2-phenyl-1,3-thiazol-5-yl)octane-1,7-dione;

9-hydroxy-9-(5-phenyl-1H-imidazol-2-yl)nonan-3-one;

9-methoxy-9-[2-(2-naphthyl)-1H-imidazol-5-yl]nonan-3-one;

9-hydroxy-9-[2-(2-naphthyl)-1H-imidazol-5-yl]nonan-3-one;

2-{1-[(anilinocarbonyl)oxy]-7-oxononyl}-5-(2-naphthyl)-1H-imidazol-1-ium trifluoroacetate;

2-(1-{[(benzylamino)carbonyl]oxy}-7-oxononyl)-5-(2-naphthyl)-1h-imidazol-1-ium trifluoroacetate;

and the pharmaceutically acceptable free bases, salts and stereoisomers thereof.

Included in the instant invention is the free base of compounds of Formula I, as well as the pharmaceutically acceptable salts and stereoisomers thereof. Some of the specific compounds exemplified herein are the protonated salts of amine compounds. Compounds of Formula I with a heterocycle ring containing 2 or more N atoms may be protonated on any one, some or all of the N atoms. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Preferably, a pharmaceutically acceptable salt of this invention contains 1 equivalent of a compound of formula (I) and 1, 2 or 3 equivalent of an inorganic or organic acid. More particularly, pharmaceutically acceptable salts of this invention are the trifluoroacetate or the chloride salts, especially the trifluoroacetate salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention can be used in a method of treatment of the human or animal body by therapy.

The compounds of the invention find use in a variety of applications for human and animal health. The compounds of the invention are histone deacetylase (HDAC) inhibitors useful in the treatment of cancer among other diseases. HDACs catalyse the removal of acetyl groups from lysine residues on proteins, including histones and HDAC inhibitors show diverse biological functions including affecting gene expression, cell differentiation, cell cycle progression, growth arrest, and/or apoptosis. See *J. Med. Chem.* 2003, 46:5097 and *Curr. Med. Chem.* 2003, 10:2343.

The compounds of the invention are used to treat cellular proliferation diseases. Disease states which can be treated by the methods and compositions provided herein include, but are not limited to, cancer (further discussed below), neurodegenerative diseases, schizophrenia and stroke The compounds, compositions and methods provided herein are particularly deemed useful for the treatment of cancer including solid tumors such as skin, breast, brain, cervical carcinomas, testicular carcinomas, etc. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Thus, the present invention provides a compound of formula I for use in the manufacture of a medicament for treating cellular proliferation diseases.

The present invention also provides a method for the treatment of cellular proliferation diseases, which method comprises administration to a patient in need thereof of an effective amount of a compound of formula I or a composition comprising a compound of formula I.

The compounds of the instant invention may also be useful in the treatment or prevention of neurodegenerative diseases, including, but not limited to, polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS). See WO 02/090534 and WO 03/083067.

Thus, the present invention provides a compound of formula I for use in the manufacture of a medicament for treating or preventing neurodegenerative diseases.

The present invention also provides a method for treating or preventing neurodegenerative diseases, which method comprises administration to a patient in need thereof of an effective amount of a compound of formula I or a composition comprising a compound of formula I.

The compounds of the invention may also be useful in the treatment or prevention of mental retardation, in particular "X chromosome-linked mental retardation" and "Rubinstein-Taybi syndrome".

Thus, the present invention provides a compound of formula I for the manufacture of a medicament for treating or preventing mental retardation.

The present invention also provides a method for treating or preventing mental retardation, which method comprises administration to a patient in need thereof of an effective amount of a compound of formula I or a composition comprising a compound of formula I.

The compounds of the invention may also be useful in the treatment or prevention of schizophrenia, see WO 02/090534.

Thus, the present invention provides a compound of formula I for the manufacture of a medicament for treating or preventing schizophrenia.

The present invention also provides a method for treating or preventing schizophrenia, which method comprises administration to a patient in need thereof of an effective amount of a compound of formula I or a composition comprising a compound of formula I.

The compounds of the invention may also be useful in the treatment or prevention of inflammatory diseases, including, but not limited to stroke, rheumatoid arthritis, lupus erythematosus, ulcerative colitis and traumatic brain injuries. See Leoni et al., *PNAS*, 99(5):2995-3000 (2002), Suuronen et al., *J. Neurochem.* 87:407-416 (2003) and *Drug Discovery Today*, 10:197-204 (2005).

Thus, the present invention provides a compound of formula I for the manufacture of a medicament for treating or preventing inflammatory diseases.

The present invention also provides a method for treating or preventing inflammatory diseases, which method comprises administration to a patient in need thereof of an effective amount of a compound of formula I or a composition comprising a compound of formula I.

The compounds of the present invention are also useful in the inhibition of smooth muscle cell proliferation and/or migration and are thus useful in the prevention and/or treatment of restenosis, for example after angioplasty and/or stent implantation.

Thus, the present invention provides a compound of formula I for the manufacture of a medicament for treating or preventing restenosis.

The present invention also provides a method for treating or prevention restenosis, which method comprises administration to a patient in need thereof of an effective amount of a compound of formula I or a composition comprising a compound of formula I.

In one embodiment, smooth muscle cell proliferation and/or migration is inhibited and restenosis is prevented and/or treated by providing a stent device having one or more of the compounds of the instant invention in or on the stent device, e.g. coated onto the stent device. The stent device is designed to controllably release the compounds of the invention, thereby inhibiting smooth muscle cell proliferation and/or migration and preventing and/or treating restenosis.

Stenosis and restenosis are conditions associated with a narrowing of blood vessels. Stenosis of blood vessels generally occurs gradually over time. Restenosis, in contrast, relates to a narrowing of blood vessels following an endovascular procedure, such as balloon angioplasty and/or stent implantation, or a vascular injury.

Balloon angioplasty is typically performed to open a stenotic blood vessel; stenting is usually performed to maintain the patency of a blood vessel after, or in combination with, balloon angioplasty. A stenotic blood vessel is opened with balloon angioplasty by navigating a balloon-tipped catheter to the site of stenosis, and expanding the balloon tip effectively to dilate the occluded blood vessel. In an effort to maintain the patency of the dilated blood vessel, a stent may be implanted in the blood vessel to provide intravascular support to the opened section of the blood vessel, thereby limiting the extent to which the blood vessel will return to its occluded state after release of the balloon catheter. Restenosis is typically caused by trauma inflicted during angioplasty, effected by, for example, balloon dilation, atherectomy or laser ablation treatment of the artery. For these procedures, restenosis occurs at a rate of about 30% to about 60% depending on the vessel location, lesion length and a number of other variables. This reduces the overall success of the relatively non-invasive balloon angioplasty and stenting procedures Restenosis is attributed to many factors, including proliferation of smooth muscle cells (SMC). SMC proliferation is triggered by the initial mechanical injury to the intima that is sustained at the time of balloon angioplasty and stent implantation. The process is characterized by early platelet activation and thrombus formation, followed by SMC recruitment and migration, and, finally, cellular proliferation and extracellular matrix accumulation. Damaged endothelial cells, SMCs, platelets, and macrophages secrete cytokines and growth factors which promote restenosis. SMC proliferation represents the final common pathway leading to neointimal hyperplasia. Therefore, anti-proliferative therapies aimed at inhibiting specific regulatory events in the cell cycle may constitute the most reasonable approach to restenosis after angioplasty.

The compounds of the invention may also be used as immunosuppressants or immunomodulators and can accordingly be used in the treatment or prevention of immune response or immune-mediated responses and diseases such as systemic lupus erythematosus (SLE) and acute or chronic transplant rejection in a recipient of an organ, tissue or cell transplant, (see WO 05/013958).

Examples of autoimmune diseases for which the compounds of the invention may be employed include autoimmune hematological disorders (including hemolytic anemia, aplastic anemia, pure red cell anemia and idiopathic thrombocytopenia), systemic lupus erythematosus, thyroiditis, Hashimoto's thyroiditis, polychondritis, scleredoma, Wegener granulomatosis, dermatomyositis, chronic active hepatitis, myasthenia gravis, psoriasis, atopic dermatitis, vasculitis, Steven-Johnson syndrome, idiopathic sprue, autoimmune inflammatory bowel disease (including ulcerative colitis and Crohn's disease) endocrine ophthalmopathy, Graves disease, sarcoidosis, multiple sclerosis, primary biliary cirrhosis, juvenile diabetes (diabetes mellitus type I), diabetes type II and the disorders associated therewith, uveitis (anterior and posterior), keratoconjunctivitis sicca and vernal keratoconjunctivitis, interstitial lung fibrosis, psoriatic arthritis, glomerulonephritis (with and without nephrotic syndrome, including idiopathic nephrotic syndrome or minimal change nephropathy), juvenile dermatomyositisinfectious, auto-antibody mediated diseases, aplastic anemia, Evan's syndrome, autoimmune hemolytic anemia, infectious diseases causing aberrant immune response and/or activation, such as traumatic or pathogen induced immune disregulation, including for example, that which are caused by hepatitis B and C infections, *staphylococcus aureus* infection, viral encephalitis, sepsis, parasitic diseases wherein damage is induced by inflammatory response (e.g. leprosy); and circulatory diseases, such as arteriosclerosis, atherosclerosis, polyarteritis nodosa and myocarditis.

Thus, the present invention provides a compound of formula I for the manufacture of a medicament for the treatment or prevention of immune disorders.

The present invention also provides a method for treating or preventing immune disorders, which method comprises administration to a patient in need thereof of an effective amount of a compound of formula I or a composition comprising a compound of formula I.

The compounds of the invention may also be useful in the treatment or prevention of other diseases such as diabetes, cardiovascular disorders and asthma.

The compounds of the invention may also be useful in the treatment or prevention of cardiac hypertrophy and heart failure, as described in *Cell*, 110:479-488 (2002).

The compounds of this invention may be administered to mammals, preferably humans, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be Administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration generally occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. Thus, this invention provides combinations of compounds of formula (I) and known therapeutic agents and/or anti-cancer agents for simultaneous, separate or sequential administration. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: other HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: other HDAC inhibitors, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Examples of "other HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin, bortezomib, epoxomicin and peptide aldehydes such as MG 132, MG 115 and PSI.

In an embodiment, the compounds of the present invention may be used in combination with other HDAC inhibitors such as SAHA and proteasome inhibitors.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycamptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 02/056880, WO 03/050,064, WO 03/050,122, WO 03/049,527, WO 03/049,679, WO 03/049,678, WO 03/039460, WO 03/079973, WO 03/099211, WO 2004/039774, WO 03/105855, WO 03/106417, WO 2004/087050, WO 2004/058700, WO 2004/058148 and WO 2004/037171 and US applications US 2004/132830 and US 2004/132719. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, neizarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin. Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR (for example those disclosed in WO 03/059951), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272, and U.S. Pat. No. 5,932,598, all of which are hereby incorporated by reference.

Inhibitors of COX-2 that are particularly useful in the instant method of treatment are 5-chloro-3-(4-methylsulfo-nyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\beta_5\alpha_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see J. Cardiovasc. Pharmacol. 1998; 31:909-913; J. Biol. Chem. 1999; 274: 9116-9121; Invest. Opthalmol. Vis. Sci. 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (Arch. Ophthamol. 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with antiviral agents (such as nucleoside analogs including ganciclovir for the treatment of cancer. See WO 98/04290.

Another embodiment of the instant invention is the use of the presently disclosed compounds in combination with gene therapy for the treatment of cancer. For an overview of genetic strategies to treating cancer see Hall et al (Am J Hum Genet. 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (J Immunol 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with a second compound selected from: other IMAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interferes with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: other HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interferes with a cell cycle checkpoint, an apoptosis inducing agent and a bisphosphonate.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: other HDAC inhibitors, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of cell proliferation and survival signaling, an agent that interferes with a cell cycle checkpoint, an apoptosis inducing agent and a bisphosphonate.

These and other aspects of the invention will be apparent from the teachings contained herein.

All patents, publications and pending patent applications identified are hereby incorporated by reference.

Abbreviations used in the description of the chemistry, in the Examples and the assays that follow are: BSA (bovine serum albumin); n-BuLi (n-butyl lithium); DCM (dichloromethane); DEA (Diethylamine); DMEM (Dulbecco's Modified Eagle Medium); DMF (dimethylformamide); DMSO (dimethyl sulfoxide); EDC.HCl (1-Ethyl-3-(3-dimethyllaminopropyl)carbodiimide hydrochloride); EDTA (ethylenediaminetetraacetic acid); em (emission); EtOAc (ethyl acetate); EtOH (ethanol); ex (exitation); HOBt (1-hydroxybenzotriazole); HPLC (high performance liquid chromatography); KCl (potassium chloride); MeCN (acetonitrile); MS (mass spectrometry); NMR (nuclear magnetic resonance); PBS (Phosphate buffered saline); RP (reverse phase); RT (room temperature); THF (tetrahydrofuran); TFA (trifluoroacteic acid); SEM-Cl ([2-(chloromethoxy)ethyl](trimethyl)silane); TBAF (Tetrabutylammonium fluoride); TBTU (2-(1H-Benzotriazole-1-yl)-1,1,3,3-tetramethyluronium tetrafluoroborate); TFAA (Trifluoroacetic anhydride); Tris-HCl (Tris Hydroxymethylaminoethane); TSA (Trichostatin A); and TsCl (para toluene sulfonyl chloride).

Compounds of formula I wherein Het is imidazole can be prepared by reacting a compound of formula IA:

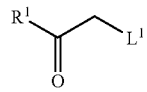

(IA)

wherein q, $R^1$, $R^2$ and $R^4$ are as defined above and $R^x$ is $C_{1-6}$alkyl group such as tert-butyl, with a cyclisation agent such as ammonium acetate. The reaction is generally carried out in a solvent such as toluene under reflux.

The dioxane protecting group can subsequently be removed using standard conditions, for example in the presence of an acid such as TFA and a solvent such as DCM at about 0° C. to room temperature.

Compounds of formula IA can be prepared by reacting a compound of formula IB with a compound of formula IC:

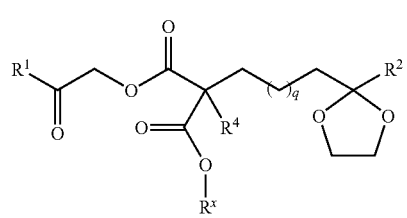

(IB)

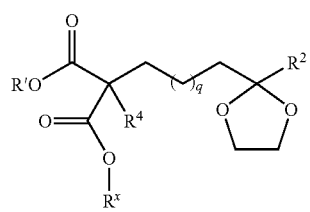

(IC)

wherein q, $R^1$, $R^2$, $R^4$ and $R^x$ are as defined above and $L^1$ is a leaving group such as halogen, for example bromine or iodine, generally in a solvent such as DMF at about room temperature. A base such as cesium carbonate in a solvent such as ethanol may also be added.

Compounds of formula IB can be prepared by hydrolysis of a compound of formula ID:

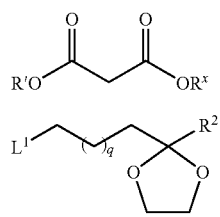

(ID)

wherein q, $R^2$, $R^4$ and $R^x$ are as defined above and R' is $C_{1-6}$alkyl, for example methyl. The reaction can generally be carried out under conventional hydrolysis conditions, for example in the presence of a base such as lithium hydroxide and solvents such as THF and water, at about room temperature.

Compounds of formula ID wherein $R^4$ is hydrogen and Y is (C=O) can be prepared by reacting a compound of formula IE with a compound of formula IF:

(IE)

(IF)

wherein q, $R^2$, R', $R^x$ and $L^1$ are as defined above, generally in a base such as sodium hydride and in a solvent such as THF at about 60° C.

Alternatively, compounds of formula I wherein Y is (C=O)$NR^7$ can be prepared by reacting a compound of formula IG with a compound of formula IH:

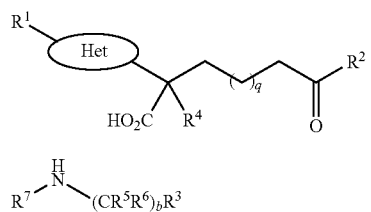

(IG)

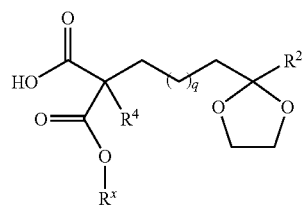

(IH)

wherein $R^1$, $R^2$, $R^3$, $R^4$, $R^5$, $R^6$, $R^7$, Het, b and q are as defined above. The reaction is generally carried out in the presence of coupling agents such as EDC.HCl and HOBt in a solvent such as DMF at about room temperature.

Compounds of formula I wherein $R^4$ together with $Y(CR^5R^6)_bR^3$ forms an oxo group can be prepared by reacting a compound of formula U with a compound of formula IK:

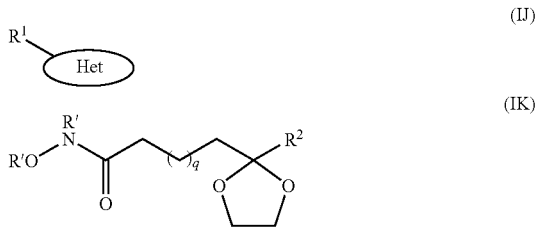

wherein $R^1$, $R^2$, Het, q and R' are as defined above. The reaction is generally carried out in the presence of an organometallic reagent such as n-BuLi, in a solvent such as THF at about −78° C. to about room temperature.

The Het ring in the compound of formula U may be protected by a protecting group when appropriate. For example, when Het is imidazole, a N ring atom may be protected by a protecting group such as SEM. The SEM group can be attached by reaction with SEM-X, wherein X is a halogen such as chlorine, in the presence of a base such as sodium hydride and a solvent such as THF at about 0° C.

The dioxane protecting group can subsequently be removed using standard conditions, for example in the presence of an acid such as TFA and a solvent such as DCM at about 0° C. to room temperature.

Compounds of formula IJ can be prepared by reacting a compound of formula IL with a compound of formula IM:

wherein $R^1$, Het and $L^1$ are as defined above. The reaction is generally carried out in the presence of a catalyst such as $PdCl_2(PPh_3)_2$ and a solvent such as benzene, in an Argon atmosphere at about 60° C.

The Het ring in the compound of formula IL may be protected by an appropriate protecting group, as described above.

Compounds of formula I wherein Y is $(CH_2)_nO$ can be prepared by reacting a compound of formula IN with a compound of formula IO:

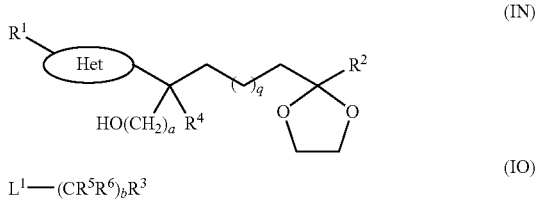

wherein $R^1$, $R^2$, $R^3$, $R^4$, $R^5$, $R^6$, Het, a, b, q and $L^1$ are as defined above. The reaction is generally carried out in the presence of a base such as sodium hydride and in a solvent such as THF at about 0° C. to room temperature.

Compounds of formula IN wherein a is 1 can be prepared by reducing a compound of formula ID, generally under standard reducing conditions such as in the presence of a reducing agent such as lithium aluminium hydride.

Where the synthesis of intermediates and starting materials is not described, these compounds are commercially available or can be made from commercially available compounds by standard methods or by extension of the Examples herein.

Compounds of formula I may be converted to other compounds of formula I by known methods or by extension of the methods described in the processes described above, the Schemes and the Examples.

Thus, the oxo group in compounds of formula I wherein $R^4$ together with $Y(CR^5R^6)_bR^3$ forms an oxo group can be reduced to a hydroxy group under standard conditions. For example, a reducing agent such as sodium borohydride may be used, in the presence of a solvent such as ethanol at about 0° C.

Compounds of formula I wherein $R^4$ is $C_{1-6}$alkyl and $Y(CR^5R^6)_bR^3$ is hydroxy can be prepared by reacting a compound of formula I wherein $R^4$ together with $Y(CR^5R^6)_bR^3$ forms an oxo group with an appropriate organometallic reagent such as R"Li or grignard reagent such as R"—MgX, wherein R" is $C_{1-6}$alkyl and X is a halogen such as bromine, generally in a solvent such as THF at about −78° C.

Compounds of formula I wherein $Y(CR^5R^6)_bR^3$ is hydroxy may be converted to a compound of formula I wherein $Y(CR^5R^6)_bR^3$ is $O(C=O)NH(CR^5R^6)_bR^3$ by reacting with an appropriate isocyanate of formula IP:

$$OCN-(CR^5R^6)_bR^3 \quad (IP)$$

wherein $R^3$, $R^5$, $R^6$ and b are as defined above, generally in the presence of a base such as pyridine and a solvent such as toluene at about 40° C.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis,* 3rd Edition, Greene, T. W. and Wuts, P. G. M.; Wiley Interscience, 1999 and Kocienski, P. J. *Protecting Groups,* Thieme, 1994. The protecting groups may be removed at a convenient subsequent stage using methods known from the art. For example, when the BoC protecting group is present, it may be removed by the addition of solvents such as TFA and DCM.

Schemes

A method to prepare compounds of formula I where Het is imidazole is shown in scheme 1. Alkylation of the tert-butyl methyl malonate with a suitable elaborated alkyl halide in the presence of a base, such as sodium hydride, gives rise to a homologated malonate derivative. Hydrolysis of the methyl ester under standard conditions, lithium hydroxide, liberates the mono-ester which can be alkylated with α-haloketone in the presence of a base, such as $Cs_2CO_3$. Upon heating in the presence of excess ammonium acetate in a high boiling solvent such as toluene formation of the imidazole occurs. Treatment with acids, such as trifluoroacetic acid, liberates the carboxylic acid and removes additional protecting groups, such as ketal protection of the carbonyl moiety. The carboxylic acid can then be coupled with amines under standard procedures, such as using EDCI and HOBt, to give amides.

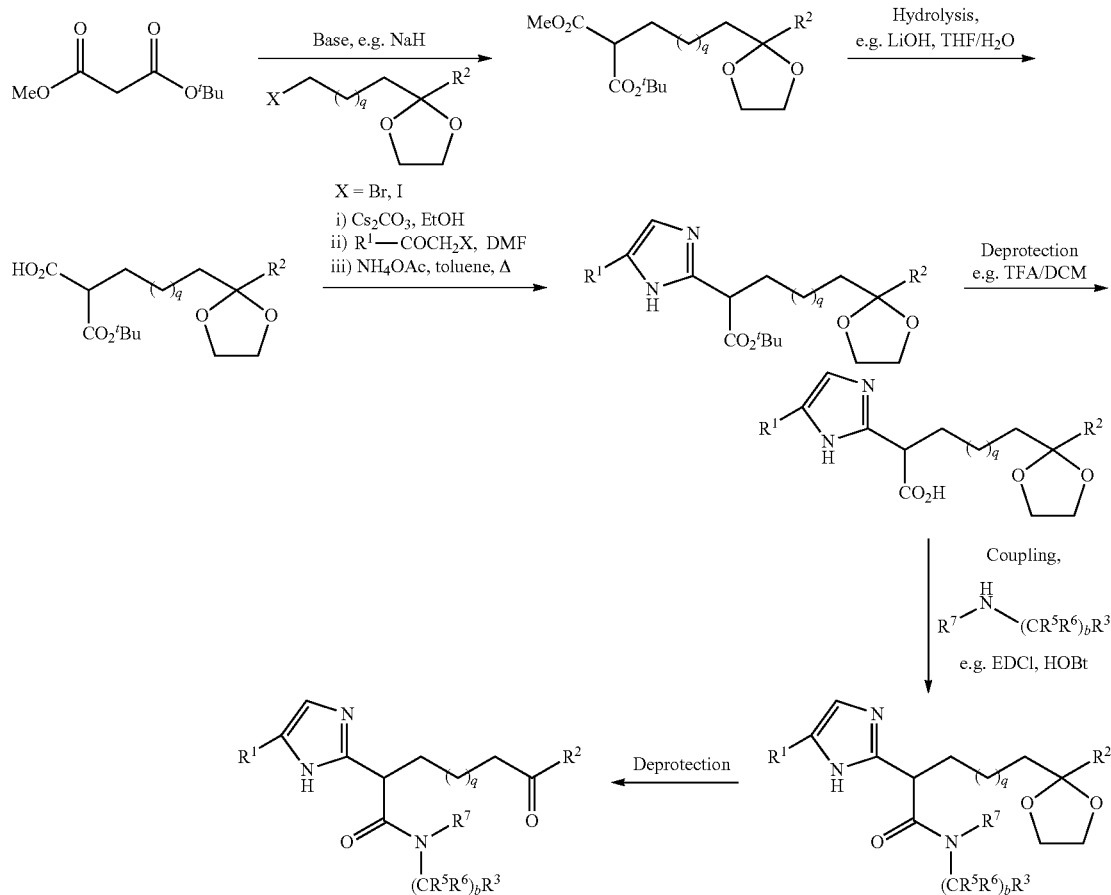

The preparation of other linkers can be made directly from the key tert-butyl ester, as shown in scheme 2. For instance, reduction of the ester can lead to, after deprotection of any protecting groups, the corresponding alcohol. Alternatively, this alcohol can be alkylated with various electrophiles, for instance alkyl halides which gives rise to esters, this sequences necessitates protection of the imidazole using a group such as a SEM-group prior to any alkylation chemistry.

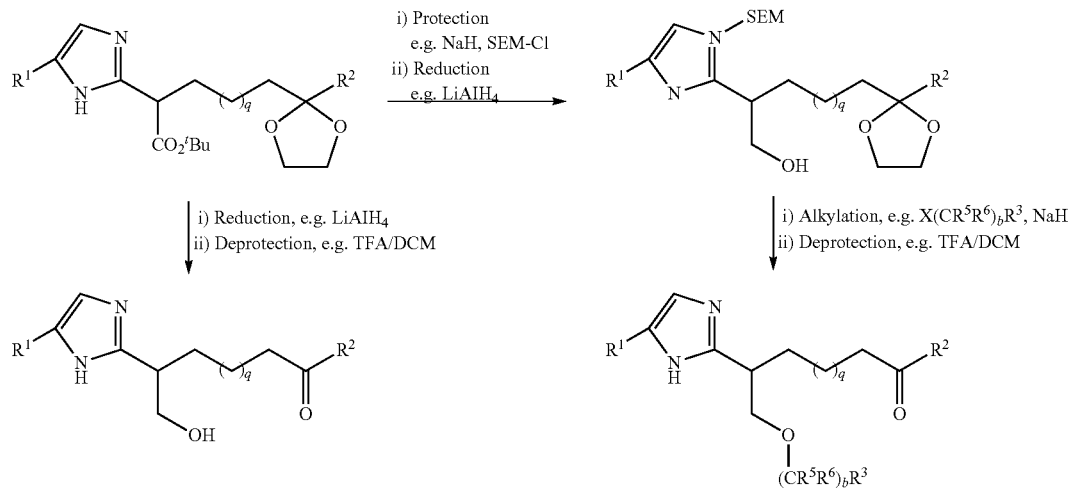

An alternative synthetic procedure is shown in scheme 3 which gives rise to carbonyl and alcohol, substituents at the heterobenzylic position of these HDAC inhibitors. For instance lithiation of a heterocyclic (appropriately protected if necessary, e.g. SEM-protecting groups) with a reagent such as n-BuLi, gives rise to a heterocyclic organometallic reagent which can be added to a Weinreb amide to yield the corresponding ketone. Treatment with acid removes any protecting groups that may be present on the heterocycle and carbonyl moiety, e.g. SEM and ketal. The intermediate heterocyclic ketone can also be reduced to the corresponding secondary alcohol with reagents such as sodium borohydride, again yielding the desired inhibitor after deprotection of the protecting groups as appropriate. In turn, these racemic mixtures of alcohols can be separated into the enantiomers by means of chiral chromatography, for instance: using super critical $CO_2$ as eluent on a chiral stationary phase.

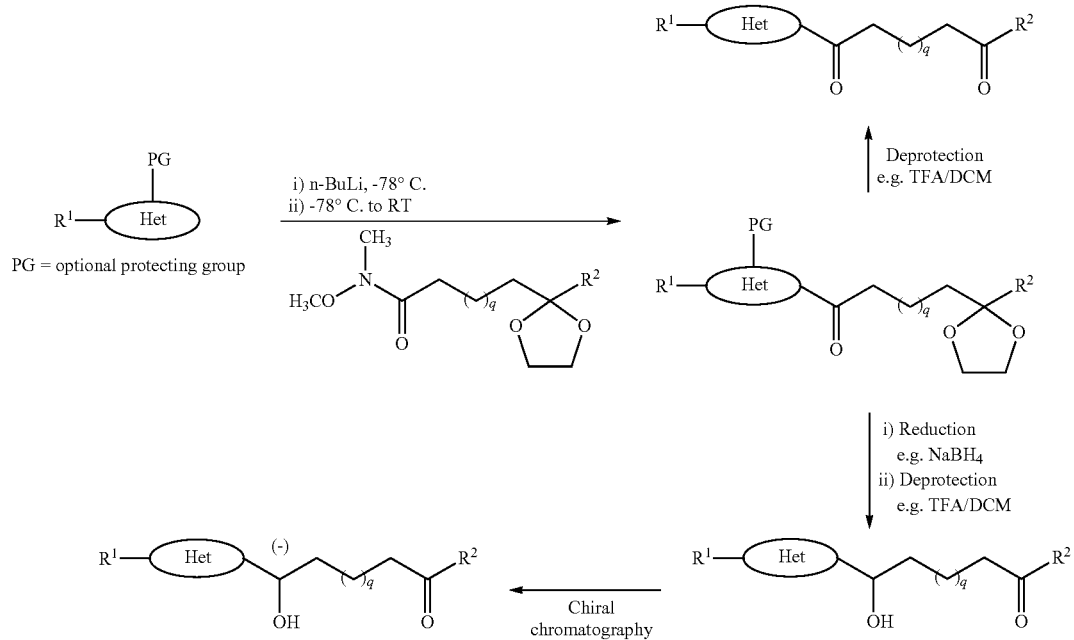

Scheme 3

A method to prepare tertiary alcohols is shown in scheme 3 whereby addition of an organometallic reagent, e.g. organolithium such as MeLi or a Grignard reagent, to the above heterocyclic ketone followed by deprotection yields the desired inhibitors.

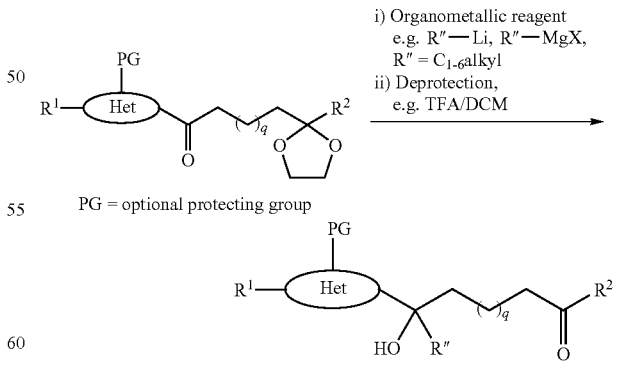

Scheme 4

Alternatively, ethers can be prepared by the alkylation of the alcohols prepared above by treatment with a base such as sodium hydride and an alkylation agent. In a related manner, carbamates can be synthesised by treatment of these alcohols with the appropriate isocyanate, as shown in scheme 5.

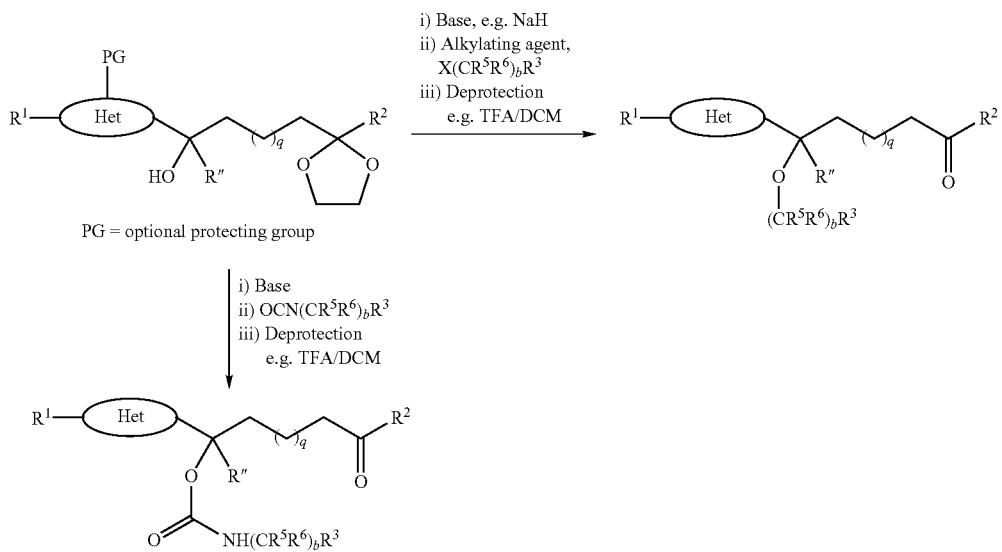

Scheme 5

The exemplified compounds described herein were tested by the assays described below and were found to have an $IC_{50}$ value of less than 10 μM.

HDAC1 Assay

Assay Description:

The HDAC1 assay is used to quantify the histone deacetylase (HDAC) activity. The assay is performed in 96 well microtiter plates by pre-incubating serial dilutions of compounds with a fixed concentration of Purified HDAC1 and then adding an acetylated lysine-containing substrate/developer that fluoresces upon deacetylation. The deacetylase reaction is performed at 37° C. for 60 min, terminated by addition of the developer solution, and then fluorescence (ex 360 nM, em 460 nM) is measured using a plate reader.

HDAC Substrate Buffer System

Reagents of the HDAC Fluorescent Activity Assay are purchased from BioMol Research Laboratories (Plymouth Meeting, Pa.) and feature the Fluor-de-Lys™ Substrate/Developer System. The reagents include the proprietary fluorescent substrate as a 50 mM stock solution (KI-104), and the Developer Concentrate (KI-105). Deacetylation of the lysine residue of the Fluor-de-Lys substrate is quantified by measuring the fluorescence (ex 360 nM, em 460 nM) after addition of the proprietary Developer.

Working Reagents:

TSA Stock: TSA is provided as a 10 mM stock solution in 100% dimethylsulfoxide (DMSO).

Assay Buffer: 25 mM Tris/HCl pH8, 137 mM NaCl, 2.7 mM KCl, 1 mM MgCl2, 0.1 mg/ml BSA Diluted Substrate Solution: The commercial 50 mM Fluor-de-Lys substrate (KI-104) is diluted to 150 uM with HDAC Assay Buffer prior to each use. The final concentration in the assay is 30 uM.

Diluted Developer Solution: The commercial 20× Developer Concentrate (KI-105) is diluted 1:167 into HDAC Assay Buffer. 2 uM [final] TSA to this solution increases its ability to stop the reaction.

HDAC1 Working Solution: The HDAC1 enzyme is diluted in assay buffer prior to each use from a fresh aliquot of enzyme. The final concentration in the assay is 1-2 nM.

Compounds: Test compounds should be prepared as a 10×5% DMSO solution in assay buffer. The final DMSO concentration in the reaction is 0.5%.

Experimental Design:

The reaction is performed in 96-well microplate in a final volume of 50 ul/well, as following:

Add 5 ul of DMSO/compound solution
Add 35 ul of HeLa HDAC1 in assay buffer (or 35 ul assay buffer in the negative controls)
Incubate 10' at room temperature
Start the reaction by adding 10 ul of the 150 uM Substrate Solution
Incubate 1 h at 37° C.
Stop by adding 50 ul of Developer/4 uM TSA solution
Incubate 10 min at room temperature
Measure the fluorescence at Ex.360 nM and Em.460 nM Extraction and Purification Protocol for Flag-Tagged HDAC1 Expressed in HeLa Cells HeLa cells transiently transfected with pcDNA3-HDAC1-FLAG are grown to 80% confluence on 10 cm culture dishes in DMEM, 10% Fetal bovine serum supplemented with antibiotics and glutamine. Cells are washed with 10 ml cold PBS and scraped into 2 ml of PBS. Cells are centrifuged for 5 minutes at 800×g at 4° C., washed with 30 ml PBS and resuspended in 10 ml PBS, counted, re-centrifuged and frozen at −80° C.

The frozen cell pellet is re-suspended in 1 ml of hypotonic lysis buffer (LB: 20 mM Hepes pH7.9, 0.25 mM EDTA, 10% glycerol) containing COMPLETE protease inhibitor and incubated on ice for 15 minutes, followed by homogenization on a 2-ml DounceB homogenizer (25 strokes). 150 mM KCl and 0.5% NP-40 are added to the homogenate and the solution is sonicated twice for 30 seconds (outputs/6, duty cycle 90) and incubated for 1 hour at 4° C. After a 30 minutes centrifugation at 12000 rpm and 4° C. the supernatant (soluble extract) is collected and protein concentration is determined using the BIORAD assay.

Anti-FLAG M2 affinity resin (Sigma) is washed three times with TBS and twice with LB. 10 μl of the LB-washed resin/mg of protein (2-3 ug of Flagged-HDAC1) are added to the soluble extract (1 mL) and incubated overnight at 4° C.

with gentle mixing. The resin is then collected by centrifugation, washed once with LB, twice with LB+0.1% NP40 and twice with elution buffer (50 mM Hepes pH 7.4, 5% glycerol, 100 mM KCl, 0.01% Triton X-100).

The affinity-purified HDAC is eluted from the resin by addition of a 10-fold excess (with respect to the resin) of elution buffer containing 100 µg/ml 3XFLAG peptide (SIGMA). The concentration of purified HDAC is determined by Western blot analysis.

Other assays are known in the literature and can be readily performed by those skilled in the art.

The following Examples illustrate the present invention.

EXAMPLE 1

2-[5-(2-Naphthyl)-1H-imidazol-2-yl]-8-oxodecanoic acid (A4)

Step 1: tert-Butyl methyl[5-(2-ethyl-1,3-dioxolan-2-yl)pentyl]malonate (A1)

To a suspension of NaH (60%, 1 eq) in THF (0.1 M solution) at 0° C. was added dropwise tert-butyl methyl malonate (1 eq.) and the resulting mixture was stirred for 1 hr at RT and then added to a solution of 2-ethyl-2-(5-iodopentyl)-1,3-dioxolane (0.9 eq) in THF (0.3 M solution). The resulting mixture was stirred at 60° C. for 1 hr and then $NH_4Cl$ solution was added and the organic layer separated, dried ($Na_2SO_4$) and concentrated under reduced pressure to yield a colorless oil which was used without any further purification. $^1H$ NMR (400 MHz, $CDCl_3$) δ: 3.81 (4H, s), 3.61 (3H, s), 3.12 (1H, t, J=7.4 Hz), 1.80-1.67 (2H, m), 1.56-1.43 (4H, m), 1.34 (9H, s), 1.29-1.17 (6H, m), 0.79 (3H, t, J=7.5 Hz). MS (ES) $C_{18}H_{32}O_6$ requires: 344, found: 367 (M+Na)$^+$.

Step 2: 2-(tert-Butoxycarbonyl)-7-(2-ethyl-1,3-dioxolan-2-yl)heptanoic acid (A2)

A solution of A1 (1 eq.) in $THF/H_2O$ (2:1, 0.09 M solution) was treated with LiOH (1.1 eq) and the solution was stirred for 3 hr at RT. The reaction was quenched with 6N HCl and the product was extracted with EtOAc. The organic layer was dried ($Na_2SO_4$) and the solvent removed under reduced pressure to yield a white solid which was used without any further purification. $^1H$ NMR (400 MHz, $CDCl_3$) δ: 3.86 (4H, s), 3.16 (1H, t, J=7.3 Hz), 1.90-1.68 (2H, m), 1.63-1.46 (4H, m), 1.39 (9H, s), 1.33-1.15 (6H, m), 0.84 (3H, t, J=7.5 Hz). MS (ES) $C_{17}H_{30}O_6$ requires: 330, found: 331 (M+H)$^+$.

Step 3: tert-Butyl 7-(2-ethyl-1,3-dioxolan-2-yl)-2-[5-(2-naphthyl)-1H-imidazol-2-yl]heptanoate(A3)

A solution of A2 (1 eq.) and $Cs_2CO_3$ (0.5 eq) in EtOH (0.47 M solution) was stirred for 45 min at RT and then concentrated under reduced pressure. 2-Bromo-1-(2-naphthyl)ethanone (1 eq.) was then added to a mixture of the resulting salt in DMF (0.27 M solution) and the mixture was stirred for 2 h at RT under $N_2$. The DMF was then removed under reduced pressure, azeotroping with toluene. EtOAc was added, the mixture was filtered and the residue washed with EtOAc, and the combined filtrates were concentrated under reduced pressure. A mixture of the resulting oil and $NH_4OAc$ (20 eq.) in toluene (0.1 M solution) was heated at reflux for 2 h and the excess $NH_4OAc$ and $H_2O$ were removed using a Dean-Stark trap. The mixture was cooled to RT, diluted with EtOAc and washed with sat. aq. $NaHCO_3$ solution and brine. The solution was dried ($Na_2SO_4$), concentrated under reduced pressure and the resulting brown oil was purified by chromatography on silica gel eluting with 20-50% EtOAc/petroleum ether to obtain the title compound as a pale brown foam. $^1H$ NMR (400 MHz, $CDCl_3$) δ: 8.15 (1H, s), 7.89-7.71 (4H, m), 7.49-7.37 (2H, m), 7.35 (1H, s), 3.97 (1H, t, J=7.2 Hz), 3.89 (4H, s), 2.06-1.87 (2H, m), 1.65-1.52 (4H, m), 1.49 (9H, s), 1.41-1.27 (6H, m), 0.87 (3H, t, J=7.5 Hz). MS (ES) $C_{29}H_{38}N_2O_4$ requires: 478, found: 479 (M+H)$^+$.

Step 4: 2-[5-(2-Naphthyl)-1H-imidazol-2-yl]-8-oxodecanoic acid (A4)

The ester (A3) was treated with TFA/DCM (3:7, 0.2 M solution) at 0° C. and then the cooling bath was removed and the mixture was stirred at RT for 4 hr. The solvents were removed under reduced pressure. The majority of the crude acid was used without further purification and a portion was purified by RP-HPLC. $^1H$ NMR (400 MHz, DMSO) δ: 8.37 (1H, s), 8.15 (1H, s), 8.12-8.03 (1H, m), 8.03-7.90 (3H, m), 7.70-7.53 (2H, m), 4.03 (1H, t, J=7.7 Hz), 2.48-2.34 (4H, m), 2.25-2.00 (2H, m), 1.58-1.42 (2H, m), 1.39-1.17 (4H, s), 0.92 (3H, t, J=7.3 Hz). MS (ES) $C_{23}H_{26}N_2O_3$ requires: 378, found: 379 (M+H)$^+$.

EXAMPLE 2

5-(2-Naphthyl)-2-(7-oxo-1-{[(2-phenylethyl)amino]carbonyl}nonyl)-1H-imidazol-1-ium trifluoroacetate (B1)

A solution of EDC.HCl (1.5 eq.), HOBt (1.5 eq.) and Example 1 (1 eq.) in DMF was stirred at RT for 30 min and then 2-phenylethylamine (1.5 eq.) was added and the mixture was stirred overnight at RT. The resulting reaction mixture was purified by preparative RP-HPLC (column: C18), using $H_2O$ (0.1% TFA) and MeCN (+0.1% TFA) as eluents, the desired fractions were lyophilized to afford the titled compound B1 as a white powder. $^1H$ NMR (400 MHz, DMSO-d6) δ: 14.45 (1H, bs), 8.55 (1H, bs), 8.41 (1H, s), 8.17 (1H, s), 8.13-8.05 (1H, m), 8.04-7.91 (3H, m), 7.68-7.57 (2H, m), 7.36-7.17 (5H, m), 4.03 (1H, t, J=7.7 Hz), 3.48-3.38 (2H, m), 2.82 (2H, t, J=8.1 Hz), 2.47-2.36 (4H, m), 2.08-1.94 (2H, m), 1.53-1.41 (2H, m), 1.30-1.05 (4H, m), 0.93 (3H, t, J=7.2 Hz). MS (ES) $C_{31}H_{35}N_3O_2$ requires: 481, found: 482 (M+H)$^+$.

EXAMPLE 3

2-[1-(Hydroxymethyl)-7-oxononyl]-5-(2-naphthyl)-1H-imidazol-1-ium trifluoroacetate (C2)

Step 1: 7-(2-Ethyl-1,3-dioxolan-2-yl)-2-[5-(2-naphthyl)-1H-imidazol-2-yl]heptan-1-ol (C1)

A solution of Example 1, A3 (1 eq.) in dry THF (0.07 M solution) was treated with $LiAlH_4$ (2.0 eq.) and the mixture was stirred at RT for 2 h, and then quenched by the addition of sat. aq. $NH_4Cl$ solution. The mixture extracted with EtOAc, the organic layer washed with brine, dried ($Na_2SO_4$) and concentrated under reduced pressure. The crude was used without any further purification. MS (ES) $C_{25}H_{32}N_2O_3$ requires: 408, found: 409 (M+H)$^+$.

Step 2: 2-[1-(Hydroxymethyl)-7-oxononyl]-5-(2-naphthyl)-1H-imidazol-3-ium trifluoroacetate (C2)

The alcohol C1 was dissolved in DCM/TFA (8:2, 0.03 M solution) and the solution was stirred for 2 hr and then the solvents were removed under reduced pressure and the crude was purified by preparative RP-HPLC (column: C18), using H$_2$O (0.1% TFA) and MeCN (+0.1% TFA) as eluents. The desired fractions were lyophilized to yield a white powder. $^1$H NMR (400 MHz, DMSO-d6) δ: 14.41 (1H, bs), 8.40 (1H, s), 8.22 (1H, s), 8.15-8.06 (1H, m), 8.03-7.92 (3H, m), 7.70-7.54 (2H, m), 3.70 (2H, d, J=5.9 Hz), 3.32-3.19 (1H, m), 2.47-2.32 (4H, m), 1.88-1.72 (2H, m), 1.56-1.40 (2H, m), 1.35-1.15 (4H, m), 0.92 (3H, t, J=7.2 Hz). MS (ES) C$_{23}$H$_{28}$N$_2$O$_2$ requires: 364, found: 365 (M+H)$^+$.

EXAMPLE 4

5-(2-Naphthyl)-2-{7-oxo-1-[(pyridin-3-ylmethoxy)methyl]nonyl}-1H-imidazol-1-ium trifluoroacetate (D3)

Step 1: tert-Butyl 7-(2-ethyl-1,3-dioxolan-2-yl)-2-(5-(2-naphthyl)-1-{[2-(trimethylsilyl)ethoxy]methyl}-1H-imidazol-2-yl)heptanoate (D1)

To a solution of Example 1, A3 in dry THF (0.06 M solution) at 0° C. was added NaH (60%, 1.5 eq.) portionwise, the resulting mixture was stirred for 1 hr and then SEM-Cl (1.5 eq.) was added dropwise. The solution was allowed to warm to RT and stirred for a further 3 hrs. The reaction was quenched by the addition of sat. aq. NH$_4$Cl solution and the mixture extracted with EtOAc. The organic layer was washed with brine, dried (Na$_2$SO$_4$) and concentrated under reduced pressure. The crude was purified by column chromatography on silica gel eluting with 20-50% EtOAc/petroleum ether to obtain D1 as a pale brown foam. $^1$H NMR (400 MHz, CDCl$_3$) δ: 8.32 (1H, s), 7.91-7.75 (5H, m), 7.49-7.37 (2H, m), 5.43 (1H, d, J=10.9 Hz), 5.26 (1H, d, J=10.9 Hz), 3.90 (4H, s), 3.86 (2H, t, J=7.4 Hz), 3.57 (1H, t, J=8.1 Hz), 2.27-2.14 (2H, m), 1.67-1.57 (4H, m), 1.49 (9H, s), 1.41-1.27 (6H, m), 0.96 (2H, t, J=7.4 Hz), 0.87 (3H, t, J=7.5 Hz), 0.07 (9H, s). MS (ES) C$_{35}$H$_{52}$N$_2$O$_5$Si requires: 608, found: 609 (M+H)$^+$.

Step 2: 7-(2-Ethyl-1,3-dioxolan-2-yl)-2-(5-(2-naphthyl)-1-{[2-(trimethylsilyl)ethoxy]methyl}-1H-imidazol-2-yl)heptan-1-ol (D2)

The ester D1 was reduced using the same procedure as in Example 3, step 1 to yield the alcohol D2. MS (ES) C$_{31}$H$_{46}$N$_2$O$_4$Si requires: 538, found: 539 (M+H)$^+$.

Step 3: 5-(2-Naphthyl)-2-{7-oxo-1-[(pyridin-3-ylmethoxy)methyl]nonyl}-1H-imidazol-3-ium trifluoroacetate (D3)

To a solution of D2 (1.0 eq.) in dry THF, was added NaH (60%, 1.3 eq.) portionwise at 0° C. The mixture was stirred for 40 min at RT and then 3-bromomethylpyridine (1.3 eq.) was added and the mixture was stirred for 1 hr at RT. The solvent was evaporated under reduced pressure and the residue was dissolved in TFA/DCM (1:1) and stirred for 3 h at RT. After evaporation of the solvent under reduced pressure, the crude product was purified by preparative RP-HPLC (column: C18), using H$_2$O (0.1% TFA) and MeCN (+0.1% TFA) as eluents. The desired fractions were lyophilized to afford D3 as a white powder. $^1$H NMR (400 MHz, CDCl$_3$) δ: 8.20 (1H, s), 8.04 (1H, s), 7.89-7.71 (4H, m), 7.67-7.37 (6H, m), 4.70-4.50 (2H, m), 4.10-3.95 (1H, m), 3.75-3.42 (2H, m), 2.48-2.22 (4H, m), 2.00-1.80 (2H, m), 1.55-1.40 (2H, m), 1.34-1.15 (4H, m), 1.00 (3H, t, J=7.5 Hz). MS (ES) C$_{29}$H$_{33}$N$_3$O$_2$ requires: 455, found: 456 (M+H)$^+$.

EXAMPLE 5

5-(2-Naphthyl)-2-(8-oxononanoyl)-1H-imidazol-1-ium trifluoroacetate (E4)

Step 1: 4-Bromo-1-{[2-(trimethylsilyl)ethoxy]methyl}-1H-imidazole (E1)

To a solution of 5-bromo-1H-imidazole (1.0 eq.) in thy THF (0.4 M solution) was added NaH (60%, 1.2 eq.) portionwise at 0° C. The mixture was stirred for 2 hr at 0° C., then SEMCl (1.2 eq.) was added and the mixture was stirred for 12 hr at RT. The reaction was quenched by the addition of sat. aq. NH$_4$Cl solution and the mixture extracted with EtOAc. The organic layer was washed with brine, dried (Na$_2$SO$_4$) and concentrated under reduced pressure. The crude was purified by column chromatography on silica gel eluting with 20-50% EtOAc/petroleum ether to obtain E1 as an oil. $^1$H NMR (300 MHz, CDCl$_3$) δ: 7.45 (1H, s), 7.00 (1H, s), 5.21 (2H, s), 3.47 (2H, t, J=8.2 Hz), 0.89 (2H, t, J=8.2 Hz), 0.00 (9H, s). MS (ES) C$_9$H$_{17}$BrN$_2$OSi requires: 276/278, found: 277/279 (M+H)$^+$.

Step 2: 4-(2-Naphthyl)-1-{[2-(trimethylsilyl)ethoxy]methyl}-1H-imidazole (E2)

To a solution of E1 (1.0 eq.) in benzene (0.1 M solution), 2-naphthylboronic acid (1.5 eq.) and sat. aq. Na$_2$CO$_3$ solution under argon was added PdCl$_2$((PPh$_3$)$_3$)$_2$. The mixture was stirred for 72 hr at 60° C., then cooled and then extracted with EtOAc. The organic layer was washed with brine, dried (Na$_2$SO$_4$) and concentrated under reduced pressure. The crude was purified by column chromatography on silica gel eluting with 20-50% EtOAc/petroleum ether to obtain E2 as yellow solid. $^1$H NMR (300 MHz, CDCl$_3$) δ: 8.31 (1H, s), 7.88-7.70 (5H, m), 7.48-7.39 (3H, m), 5.28 (2H, s), 3.54 (2H, t, J=8.2 Hz), 0.94 (2H, t, J=8.2 Hz), 0.00 (9H, s). MS (ES) C$_{19}$H$_{24}$N$_2$OSi requires: 324, found: 325 (M+H)$^+$.

Step 3: 7-(2-Methyl-1,3-dioxolan-2-yl)-1-(4-(2-naphthyl)-1-{[2-(trimethylsilyl)ethoxy]methyl}-1H-imidazol-2-yl)heptan-1-one (E3)

To a solution of E2 (1.0 eq.) in THF (0.1 M solution) at −78° C. was added a solution of n-BuLi (1.3 eq.) in hexane. The solution was stirred for 30 min and then a solution of N-methoxy-N-methyl-7-(2-methyl-1,3-dioxolan-2-yl)heptanamide (1.5 eq.) in THF was slowly added. The reaction mixture was stirred for 1 hr at −78° C. and then 1 hr at RT. Then water was added and the aqueous phase was extracted with EtOAc. The combined organic extracts were dried (MgSO$_4$) and the solvent was removed under reduced pressure. The crude was purified by column chromatography on silica gel eluting with 20-50% EtOAc/petroleum ether to obtain E3 as yellow solid. $^1$H NMR (300 MHz, CDCl$_3$) δ: 8.32 (1H, s), 7.96-7.81 (4H, m), 7.68 (1H, s) 7.53-7.42 (2H, m), 5.85 (2H, s), 3.92 (4H, s), 3.64 (2H, t, J=8.2 Hz), 3.26 (2H, t, J=8.2 Hz), 1.77 (2H, m), 1.69-1.36 (8H, m), 1.31 (3H, s), 0.97 (2H, t, J=8.2 Hz), 0.19 (9H, s). MS (ES) C$_{30}$H$_{42}$N$_2$O$_4$Si requires: 522, found: 523 (M+H)$^+$.

Step 4: 1-[5-(2-Naphthyl)-1H-imidazol-2-yl]nonane-1,8-dione (E4)

The ketone E3 was dissolved in TFA/DCM (1:1) and stirred for 4 hr at RT. After evaporation of the solvent under reduced pressure, the crude product was purified by preparative RP-HPLC (column: C18), using H$_2$O (0.1% TFA) and MeCN (+0.1% TFA) as eluents. The desired fractions were lyophilized to afford E4 as a white solid. $^1$H NMR (300 MHz, DMSO) δ: 8.17 (1H, s), 7.92-7.79 (3H, m), 7.76-7.64 (2H, m), 7.55-7.45 (2H, m), 3.15 (2H, t, J=7.4 Hz), 2.44 (2H, t, J=7.4 Hz), 2.15 (3H, s), 1.74 (2H, m), 1.58 (2H, m), 1.37 (4H, m). MS (ES) C$_{22}$H$_{24}$N$_2$O$_2$ requires: 348, found: 349 (M+H)$^+$.

EXAMPLE 6

9-Hydroxy-9-[5-(2-naphthyl)-1H-imidazol-2-yl] nonan-3-one (F3)

Step 1: 6-(2-ethyl-1,3-dioxolan-2-yl)-1-(4-(2-naphthyl)-1-{[2-(trimethylsilyl)ethoxy]methyl}-1H-imidazol-2-yl)hexan-1-one (F1)

To a solution of Example 5, E2 (1.0 eq.) in THF (0.1 M solution) at −78° C. was added a solution of n-BuLi (1.3 eq.) in hexane. The solution was stirred for 30 min and then a solution of 6-(2-ethyl-1,3-dioxolan-2-yl)-N-methoxy-N-methylhexanamide (1.5 eq.) in THF was slowly added. The reaction mixture was stirred for 1 hr at −78° C. and then 1 hr at RT. Then water was added and the aqueous phase was extracted with EtOAc. The combined organic extracts were dried (MgSO$_4$) and the solvent was removed under reduced pressure. The crude product was used without purification in the next step. MS (ES) C$_{30}$H$_{42}$N$_2$O$_4$Si requires: 523, found: 524 (M+H)$^+$.

Step 2: 6-(2-ethyl-1,3-dioxolan-2-yl)-1-(4-(2-naphthyl)-1-{[2-(trimethylsilyl)ethoxy]methyl}-1H-imidazol-2-yl)hexan-1-ol (F2)

To a solution of the ketone F1 in EtOH (0.04 M solution) at 0° C. was added NaBH$_4$ (2.0 eq.) and the mixture was stirred for 1 hr. Water was slowly added and the aqueous phase was extracted with EtOAc. The combined organic extracts were dried (MgSO$_4$) and solvents were removed under reduced pressure. The crude product was used without purification in the next step. MS (ES) C$_{30}$H$_{44}$N$_2$O$_4$Si requires: 525, found: 526 (M+H)$^+$.

Step 3: 9-Hydroxy-9-[5(2-naphthyl)-1H-imidazol-2-yl]nonan-3-one (F3)

The alcohol F2 was dissolved in TFA/DCM (1:1) and stirred for 4 hr at RT. The reaction was quenched with sat. aq. NaHCO$_3$ solution and the aqueous phase was extracted with EtOAc. The combined organic extracts were dried (MgSO$_4$) and solvent was removed under reduced pressure. The crude product was purified by flash chromatography, using EtOAc/petroleum ether as eluents and the product was obtained as a white solid. $^1$H NMR (300 MHz, DMSO) δ: 8.30 (1H, s), 7.97-7.75 (6H, m), 7.58-7.41 (2H, m), 5.81 (1H, br s), 4.75 (1H, m), 2.37 (4H, m), 1.80 (2H, m), 1.51-1.19 (6H, m), 0.88 (3H, t, J=7.3 Hz). MS (ES) C$_{22}$H$_{26}$N$_2$O$_2$ requires: 350, found: 351 (M+H)$^+$.

EXAMPLE 7

(−)-9-Hydroxy-9-[5-(2-naphthyl)-1H-imidazol-2-yl] nonan-3-one (G1)

The enantiomers of Example 6, F2 were separated by super critical fluid chromatography on a chiral column (column: Chiralcel OJ-H, flow: 9.99 ml/min, modifier: 30% of MeOH with 0.2% DEA, T$_{col}$=35° C., P$_{col}$=100 bar).

The (+)-alcohol was dissolved in TFA/DCM (1:1) and stirred for 4 hr at RT. The reaction was quenched with sat. aq. NaHCO$_3$ solution and the aqueous phase was extracted with EtOAc. The combined organic extracts were dried (MgSO$_4$) and solvent was removed under reduced pressure. The crude product was purified by flash chromatography, using EtOAc/petroleum ether as eluents and G1 was obtained as a white solid. [α]$_D^{22}$=−12.6 (c=1.0 in EtOAc). MS (ES) C$_{22}$H$_{26}$N$_2$O$_2$ requires: 350, found: 351 (M+H)$^+$.

EXAMPLE 8

2-(1-Hydroxy-1-methyl-7-oxononyl)-5-(2-naphthyl)-1H-imidazol-1-ium trifluoroacetate (H1)

To a solution of Example 6, F1 (1.0 eq.) in THF (0.03 M solution) at −78° C. under argon was added methyl lithium (1.2 eq.). After 2 hr water was added and the aqueous phase was extracted with EtOAc. The combined organic extracts were dried (MgSO$_4$) and the solvent was removed under reduced pressure.

The residue was dissolved in TFA/DCM (1:1) and stirred for 4 hr. The solvent was removed under reduced pressure. The desired material was isolated by preparative RP-HPLC, using H$_2$O (+0.1% TFA) and MeCN (+0.1% TFA) as eluents (C18 column). The desired fractions were lyophilized to afford H1 as a white solid. $^1$H NMR (300 MHz, CDCl$_3$) δ: 8.23 (1H, s), 7.86-7.29 (8H, m), 2.26 (4H, m), 2.07-1.80 (2H, m), 1.63 (3H, s), 1.45-1.06 (6H, m), 0.95 (3H, t, J=7.5 Hz). MS (ES) C$_{23}$H$_{29}$N$_2$O$_2$ requires: 365, found: 365 (M)$^+$.

EXAMPLE 9

2-(1-Methoxy-7-oxononyl)-5-(2-naphthyl)-1H-imidazol-1-ium trifluoroacetate (I1)

To a solution of Example 6, F2 (1.0 eq.) in THF at 0° C. was added NaH (60%, 2.5 eq.) and after 5 min MeI (2.0 eq.) was added and the reaction mixture was stirred for 12 h. Then the solvents were removed under reduced pressure and the residue was dissolved in TFA/DCM (1:1) and stirred for 4 hr. The reaction was quenched with sat. aq. NaHCO$_3$ solution and the aqueous phase was extracted with EtOAc. The combined organic extracts were dried (MgSO$_4$) and solvent was removed under reduced pressure. The desired material was isolated by preparative RP-HPLC, using H$_2$O (+0.1% TFA) and MeCN (+0.1% TFA) as eluents (C18 column), the desired fractions were lyophilized to afford the imidazole as a white solid. $^1$H NMR (300 MHz, CDCl$_3$) δ: 8.23 (1H, s), 7.89-7.73 (3H, m), 7.59 (1H, d, J=8.8 Hz), 7.52-7.39 (3H, m), 4.68 (1H, m), 3.24 (3H, s), 2.30 (4H, m), 1.85 (2H, m), 1.42 (2H, m), 1.32-1.09 (4H, m), 0.88 (3H, t, J=7.3 Hz). MS (ES) C$_{23}$H$_{28}$N$_2$O$_2$ requires: 365, found: 366 (M+H)$^+$.

EXAMPLE 10

5-(2-Naphthyl)-2-{7-oxo-1-[({[(1S)-1-phenylethyl] amino}carbonyl)oxy]nonyl}-1H-imidazol-1-ium trifluoroacetate (H1)

To a solution of Example 6, F2 (1.0 eq.) in toluene was added (S)-methylbenzylisocyanate (1.3 eq.) and pyridine (0.2 eq.) and the reaction mixture was stirred for 60 hr at 40° C. Water was added and the aqueous phase was extracted with EtOAc. The combined organic extracts were dried (MgSO$_4$)

and then the solvent was removed under reduced pressure. The crude residue was dissolved in TFA/DCM (1:1) and stirred for 4 hr at RT. The solvent was removed under reduced pressure and the desired material was isolated by preparative RP-HPLC, using $H_2O$ (+0.1% TFA) and MeCN (+0.1% TFA) as eluents (C18 column). The desired fractions were lyophilized to afford the imidazole as a white solid. $^1H$ NMR (300 MHz, $CDCl_3$) δ: 8.05 (0.5H, s), 7.97 (0.5H, s), 7.71 (3H, m), 7.53-7.03 (9H, m), 6.99 (0.5H, d, J=7.3 Hz), 6.68 (0.5H, d, J=7.3 Hz), 5.95 (1H, m), 4.69 (1H, m), 2.29 (4H, m), 1.93 (2H, m), 1.54-1.09 (10H, m), 0.99 (1.5H, t, J=7.3 Hz), 0.97 (1.5H, t, J=7.3 Hz). MS (ES) $C_{31}H_{35}N_3O_3$ requires: 498, found: 499 $(M+H)^+$.

The following Examples were prepared according to the procedures described in Examples 1 to 10 and in the general processes and schemes described above.

| Example | Compound Name | Mass Seen $(M + H)^+$ | Procedure according to Example |
|---|---|---|---|
| 11 | 2-[1-(Anilinocarbonyl)-7-oxononyl]-5-(2-naphthyl)-1H-imidazol-1-ium trifluoroacetate | 454 | 2 |
| 12 | 2-{1-[(Benzylamino)carbonyl]-7-oxononyl}-5-(2-naphthyl)-1H-imidazol-1-ium trifluoroacetate | 468 | 2 |
| 13 | 1-Methyl-4-{2-[5-(2-naphthyl)-1H-imidazol-1-ium-2-yl]-8-oxodecanoyl}piperazin-1-ium bis(trifluoroacetate) | 461 | 2 |
| 14 | 4-{2-[5-(2-Naphthyl)-1H-imidazol-1-ium-2-yl]-8-oxodecanoyl}-1-phenylpiperazin-1-ium bis(trifluoroacetate) | 523 | 2 |
| 15 | 2-(1-{[Methyl(quinolin-6-ylmethyl)amino]carbonyl}-7-oxononyl)-5-(2-naphthyl)-1H-imidazol-1-ium trifluoroacetate | 533 | 2 |
| 16 | 1-[2-({2-[5-(2-Naphthyl)-1H-imidazol-1-ium-2-yl]-8-oxodecanoyl}amino)ethyl]piperidinium bis(trifluoroacetate) | 489 | 2 |
| 17 | 1-Benzyl-4-({2-[5-(2-naphthyl)-1H-imidazol-1-ium-2-yl]-8-oxodecanoyl}amino)piperidinium bis(trifluoroacetate) | 551 | 2 |
| 18 | 2-[1-({[2-(3,4-Dihydroquinolin-1(2H)-yl)ethyl]amino}carbonyl)-7-oxononyl]-5-(2-naphthyl)-1H-imidazol-1-ium trifluoroacetate | 537 | 2 |
| 19 | 1-[1,1-Dimethyl-2-({2-[5-(2-naphthyl)-1H-imidazol-1-ium-2-yl]-8-oxodecanoyl}amino)ethyl]piperidinium bis(trifluoroacetate) | 517 | 2 |
| 20 | 5-(2-Naphthyl)-2-(7-oxo-1-{[(1,3-thiazol-2-ylmethyl)amino]carbonyl}nonyl)-1H-imidazol-1-ium trifluoroacetate | 475 | 2 |
| 21 | 5-(2-Naphthyl)-2-(7-oxo-1-{[(pyridin-3-ylmethyl)amino]carbonyl}nonyl)-1H-imidazol-1-ium trifluoroacetate | 469 | 2 |
| 22 | 5-(2-Naphthyl)-2-{7-oxo-1-[(pyridin-3-ylamino)carbonyl]nonyl}-1H-imidazol-1-ium trifluoroacetate | 455 | 2 |
| 23 | 5-(2-Naphthyl)-2-{7-oxo-1-[(1,3-thiazol-2-ylamino)carbonyl]nonyl}-1H-imidazol-1-ium trifluoroacetate | 461 | 2 |
| 24 | 5-(2-Naphthyl)-2-(7-oxo-1-{[(pyridin-4-ylethyl)amino]carbonyl}nonyl)-1H-imidazol-1-ium trifluoroacetate | 483 | 2 |
| 25 | 5-(2-Naphthyl)-2-(7-oxo-1-{[(2-pyridin-2-ylethyl)amino]carbonyl}nonyl)-1H-imidazol-1-ium trifluoroacetate | 483 | 2 |
| 26 | 4-[2-({2-[5-(2-Naphthyl)-1H-imidazol-1-ium-2-yl]-8-oxodecanoyl}amino)ethyl]morpholin-4-ium bis(trifluoroacetate) | 491 | 2 |
| 27 | 1-[2-({2-[5-(2-Naphthyl)-1H-imidazol-1-ium-2-yl]-8-oxodecanoyl}amino)ethyl]-1H-pyrazol-1-ium bis(trifluoroacetate) | 472 | 2 |
| 28 | 4-[2-({2-[5-(2-Naphthyl)-1H-imidazol-1-ium-2-yl]-8-oxodecanoyl}amino)ethyl]-1H-pyrazol-1-ium bis(trifluoroacetate) | 472 | 2 |
| 29 | 1-Methyl-3-[({2-[5-(2-naphthyl)-1H-imidazol-1-ium-2-yl]-8-oxodecanoyl}amino)methyl]piperidinium bis(trifluoroacetate) | 489 | 2 |
| 30 | 1-Methyl-4-[({2-[5-(2-naphthyl)-1H-imidazol-1-ium-2-yl]-8-oxodecanoyl}amino)methyl]piperidinium bis(trifluoroacetate) | 489 | 2 |
| 31 | 1-Methyl-2-[(methyl{2-[5-(2-naphthyl)-1H-imidazol-1-ium-2-yl]-8-oxodecanoyl}amino)methyl]piperidinium bis(trifluoroacetate) | 503 | 2 |
| 32 | 2-[1-({[[(1-Methylpyrrolidinium-3-yl)methyl]amino}carbonyl)-7-oxononyl]-5-(2-naphthyl)-1H-imidazol-1-ium bis(trifluoroacetate) | 475 | 2 |
| 33 | 2-(1-{[(2-Methoxyethyl)amino]carbonyl}-7-oxononyl)-5-(2-naphthyl)-1H-imidazol-1-ium trifluoroacetate | 436 | 2 |
| 34 | 2-[1-({[2-(Dimethylammonio)ethyl]amino}carbonyl)-7-oxononyl]-5-(2-naphthyl)-1H-imidazol-1-ium bis(trifluoroacetate) | 449 | 2 |
| 35 | 2-[1-({[2-(Acetylamino)ethyl]amino}carbonyl)-7-oxononyl]-5-(2-naphthyl)-1H-imidazol-1-ium trifluoroacetate | 463 | 2 |
| 36 | 4-[2-({2-[5-(2-Naphthyl)-1H-imidazol-1-ium-2-yl]-8-oxodecanoyl}amino)ethyl]-4H-1,2,4-triazol-4-ium bis(trifluoroacetate) | 473 | 2 |
| 37 | 5-(2-Naphthyl)-2-(7-oxo-1-{[(2-pyrrolidinium-1-ylethyl)amino]carbonyl}nonyl)-1H-imidazol-1-ium bis(trifluoroacetate) | 475 | 2 |
| 38 | 1-Methyl-4-({2-[5-(2-naphthyl)-1H-imidazol-1-ium-2-yl]-8-oxodecanoyl}amino)piperidinium bis(trifluoroacetate) | 475 | 2 |
| 39 | 5-(2-Naphthyl)-2-[7-oxo-1-(1,3-thiazolidin-3-ylcarbonyl)nonyl]-1H-imidazol-1-ium trifluoroacetate | 450 | 2 |
| 40 | 5-(2-Naphthyl)-2-(7-oxo-1-{[(2-pyridin-3-ylethyl)amino]carbonyl}nonyl)-1H-imidazol-1-ium trifluoroacetate | 483 | 2 |
| 41 | 2-[1-(Aminocarbonyl)-7-oxononyl]-5-(2-naphthyl)-1H-imidazol-1-ium trifluoroacetate | 378 | 2 |
| 42 | 2-{1-[(Methylamino)carbonyl]-7-oxononyl}-5-(2-naphthyl)-1H-imidazol-1-ium trifluoroacetate | 392 | 2 |
| 43 | 1-(2-Phenyl-1,3-thiazol-5-yl)octane-1,7-dione | 302 | 6 |
| 44 | 9-Hydroxy-9-(5-phenyl-1H-imidazol-2-yl)nonan-3-one | 301 | 6 |
| 45 | 9-Methoxy-9-[2-(2-naphthyl)-1H-imidazol-5-yl]nonan-3-one | 365 | 9 |
| 46 | 9-Hydroxy-9-[2-(2-naphthyl)-1H-imidazol-5-yl]nonan-3-one | 351 | 5 |
| 47 | 2-{1-[(Anilinocarbonyl)oxy]-7-oxononyl}-5-(2-naphthyl)-1H-imidazol-1-ium trifluoroacetate | 471 | 10 |
| 48 | 2-(1-{[(Benzylamino)carbonyl]oxy}-7-oxononyl)-5-(2-naphthyl)-1h-imidazol-1-ium trifluoroacetate | 485 | 10 |

The invention claimed is:
1. A compound of formula I:

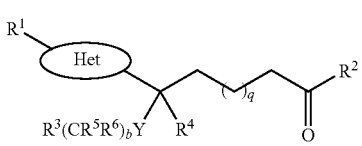

wherein:
b is 0, 1, 2, 3, 4 or 5;
q is 1, 2, 3 or 4;
Y is C=O, (C=O)NR$^7$, O(C=O)NR$^7$ or (CH$_2$)$_a$O;
a is 0, 1, 2 or 3;
Het is imidazolyl, oxazolyl, thienyl, thiazolyl or pyrazolyl optionally substituted by one or more groups independently chosen from cyano, halogen, hydroxy, oxo, nitro, amino, C$_{1-6}$alkylamino, di(C$_{1-6}$alkyl)amino, C$_{1-6}$alkyl, haloC$_{1-6}$alkyl, C$_{1-6}$alkoxy, haloC$_{1-6}$alkoxy, C$_{3-10}$cycloalkyl, C$_{2-6}$alkenyl, C$_{2-6}$alkynyl and C$_{6-10}$aryl;
R$^1$ is hydrogen, C$_{1-6}$alkyl, haloC$_{1-6}$alkyl, C$_{6-10}$aryl, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-10 membered unsaturated or partially saturated heterocycle containing heteroatoms independently selected from O, N and S; any of which rings being optionally substituted by one or more groups independently chosen from cyano, halogen, nitro, oxo, hydroxy, C$_{1-6}$alkyl, haloC$_{1-6}$alkyl, C$_{1-6}$alkoxy, haloC$_{1-6}$alkoxy, C$_{1-6}$alkylcarbonyl, C$_{1-6}$alkoxycarbonyl, carboxy, C$_{6-10}$aryl, C$_{6-10}$aryloxy, C$_{6-10}$arylcarbonyl and N(R$^a$)$_2$ wherein R$^a$ is independently selected from hydrogen, C$_{1-6}$alkyl, C$_{6-10}$aryl, C$_{1-6}$alkylcarbonyl and C$_{6-10}$arylcarbonyl;
R$^2$ is C$_{1-6}$alkyl;
R$^3$ is hydrogen, halogen, hydroxy, cyano, C$_{1-6}$alkyl, haloC$_{1-6}$alkyl, C$_{1-6}$alkoxy, haloC$_{1-6}$alkoxy, C$_{3-10}$cycloalkyl, haloC$_{3-10}$cycloalkyl, C$_{2-10}$alkenyl, C$_{2-10}$alkynyl, nitro, N(R$^d$)$_2$ wherein R$^d$ is independently selected from hydrogen, C$_{1-6}$alkyl and C$_{1-6}$alkylcarbonyl; C$_{6-10}$aryl, C$_{6-10}$arylC$_{1-6}$alkyl, C$_{6-10}$arylC$_{1-6}$alkoxy, 4, 5 or 6 membered saturated or partially saturated heterocycle containing 1, 2 or 3 heteroatoms independently selected from N, O and S, optionally bridged by a C$_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independently selected from N, O or S; any of which rings being optionally substituted by one or more groups independently chosen from R$^b$;
R$^4$ is hydrogen or C$_{1-6}$alkyl; or
R$^5$ and R$^6$ are independently hydrogen or C$_{1-6}$alkyl;
R$^7$ is hydrogen or C$_{1-6}$alkyl;
each R$^b$ is halogen, hydroxy, cyano, C$_{1-6}$alkyl, haloC$_{1-6}$alkyl, haloC$_{1-6}$alkylcarbonyl, haloC$_{1-6}$alkylcarbonyloxy, C$_{1-6}$alkoxy, haloC$_{1-6}$alkoxy, carboxy, C$_{1-6}$alkylcarbonyl, C$_{1-6}$alkoxycarbonyl, nitro, oxo, SO$_2$N(R$^c$)$_2$, N(R$^c$)$_2$ wherein R$^c$ is independently selected from hydrogen, C$_{1-6}$alkyl, C$_{1-6}$alkylcarbonyl, carboxy and C$_{1-6}$alkoxycarbonyl, or C$_{6-10}$aryl, C$_{6-10}$arylC$_{1-6}$alkyl, 5 or 6 membered saturated or partially saturated heterocycle containing 1, 2 or 3 heteroatoms independently selected from N, O or S, optionally bridged by a C$_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, C$_{1-6}$alkyl, haloC$_{1-6}$alkyl, C$_{1-6}$alkoxy and haloC$_{1-6}$alkoxy;
or a pharmaceutically acceptable salt or tautomer thereof.

2. The compound of claim 1 of formula II:

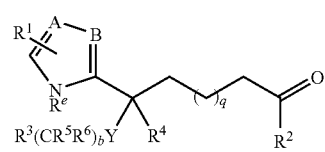

wherein:
b, q, R$^1$, R$^2$, R$^3$, R$^4$, R$^5$, R$^6$ and Y are as defined in claim 1;
one of A and B is N and the other CH;
R$^e$ is hydrogen or C$_{1-6}$alkyl;
or a pharmaceutically acceptable salt or tautomer thereof.

3. The compound of claim 1 wherein Y is C=O, (C=O)NH, (C=O)NMe, O(C=O)NH, O or (CH$_2$)O.

4. The compound of claim 1 of formula III:

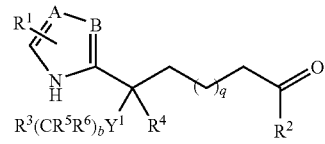

wherein:
Y$^1$ is (C=O) or (C=O)NR$^7$;
R$^1$, R$^2$, R$^3$, R$^5$, R$^6$, b and q are as defined in claim 1;
one of A and B is N and the other CH;
R$^4$ is hydrogen or C$_{1-6}$alkyl;
or a pharmaceutically acceptable salt or tautomer thereof.

5. The compound of claim 1 wherein R$^1$ is an optionally substituted ring selected from C$_{6-10}$aryl, a 5 membered unsaturated heterocycle containing 1, 2 or 3 heteroatoms independently selected from N, O and S, but not more than one of which is O or S, a 6 membered unsaturated heterocycle containing 1, 2 or 3 nitrogen atoms, or a 8, 9 or 10 membered unsaturated or partially saturated heterocycle containing 1, 2, 3 or 4 heteroatoms independently selected from O, N and S.

6. The compound of claim 1 wherein:
R$^3$ is hydrogen, dimethylamino, phenyl, naphthyl, pyrrolidinyl, piperidinyl, azoniabicyclo[2.2.1]heptanyl, azoniabicyclo[2.2.2]octanyl, piperazinyl, morpholinyl, thienyl, thiazolyl, imidazolyl, pyrazolyl, isoxazolyl, thiadiazolyl, pyridinyl, indolyl, benzothienyl, benzothiadiazolyl, benzoxadiazolyl, dihydrobenzofuryl, dihydrothiazolopyrimidinyl, isoquinolyl, dihydrobenzodioxinyl, dihydrobenzoxazinyl, tert-butoxy, cyclopentyl, methyl, trifluoromethyl, methoxy, diethylamino, hydroxy, benzimidazolyl, benzofuranyl, triazolopyrimidinyl, dihydrobenzoxazolyl, dihydroindolyl, dihydroquinazolinyl, dihydrophthalazinyl, indazolyl, quinolinyl, benzisoxazolyl, benzotriazolyl, tetrahydrobetacarbolinyl, dihydroisoindolyl, tetrahydronaphthyridinyl, tetrazolyl, benzyloxy, thiomorpholinyl, azetidinyl, tetrahydroquinolinyl, acetylamino, triazolyl, thiazolidinyl or amino; any of which rings being optionally substituted by one or more groups independently chosen from $R^b$; and $R^b$ is halogen, cyano, $C_{1-6}$alkyl, $C_{1-6}$alkoxy, haloC$_{1-6}$alkoxy, carboxy, $C_{1-6}$alkoxycarbonyl, nitro, aminosulfonyl, ($C_{1-6}$alkylcarbonyl)amino, morpholinyl, piperazinyl, thiazolyl, pyrazolyl, isoxazolyl, pyridinyl, oxo, haloC$_{1-6}$alkyl, phenyl, pyrrolidinyl or benzyl; any of which rings being optionally substituted by one or more groups independently chosen from $C_{1-6}$alkyl and haloC$_{1-6}$alkyl.

7. A pharmaceutical composition comprising a compound of claim 1, or a pharmaceutically acceptable salt or tautomer thereof and a pharmaceutically acceptable carrier.

\* \* \* \* \*